United States Patent
Goldsmith et al.

(10) Patent No.: US 12,295,943 B2
(45) Date of Patent: May 13, 2025

(54) APIXABAN DOSING

(71) Applicant: Closed Loop Medicine Ltd., Cambridge (GB)

(72) Inventors: Paul Goldsmith, London (GB); Bruce Campbell, Cambridge (GB); Michael Catt, Wellingborough (GB)

(73) Assignee: Closed Loop Medicine Ltd, Cambridge (GB)

(*) Notice: Subject to any disclaimer, the term of this patent is extended or adjusted under 35 U.S.C. 154(b) by 0 days.

(21) Appl. No.: 18/472,660

(22) Filed: Sep. 22, 2023

(65) Prior Publication Data

US 2025/0099441 A1 Mar. 27, 2025

(51) Int. Cl.
*A61K 31/437* (2006.01)
*A61P 7/02* (2006.01)

(52) U.S. Cl.
CPC ............. *A61K 31/437* (2013.01); *A61P 7/02* (2018.01)

(58) Field of Classification Search
CPC ........................................................ A61P 7/02
See application file for complete search history.

(56) References Cited

U.S. PATENT DOCUMENTS

| 6,942,614 | B1 | 9/2005 | Kutzko et al. |
| 2013/0179184 | A1 | 7/2013 | Hurst |
| 2016/0300037 | A1 | 10/2016 | Mould |

FOREIGN PATENT DOCUMENTS

| DE | 102006028232 | 12/2007 |
| WO | 2001093762 | 12/2001 |
| WO | 2005041105 | 5/2005 |
| WO | 2012079576 | 6/2012 |
| WO | 2015085276 | 6/2015 |

OTHER PUBLICATIONS

Lanau et al., Direct oral anticoagulants and its implications in dentistry. A review of literature, J. Clin. Exp. Dent., 2017, 9(11), pp. e1346-e1354 (Year: 2017).*
"Annex I Summary of Product Characteristics", Eliquis 2.5 mg film-coated tablests apixaban package leaflet, 88 pages.
"Clinical Pharmacology and Biopharmaceutics Review(S)", Center for Drug Evaluation and Research, Application No. 202155Orig1s000, Addendum to previous Review—DARRTS, Feb. 15, 2012, 220 pages.

(Continued)

*Primary Examiner* — Savitha M Rao
*Assistant Examiner* — Andrew P Lee
(74) *Attorney, Agent, or Firm* — Henry Patent Law Firm PLLC

(57) ABSTRACT

A method for administering a dosage of Apixaban to a patient for the treatment or prevention of thrombosis, the method comprising: administering a dosage of Apixaban to the patient, wherein the dosage of apixaban is determined by: receiving patient data relating to a patient, wherein the patient data includes a kidney function metric of the patient; and processing, using one or more processors, the patient data with a dosage calculator to determine the dosage of Apixaban for the patient, wherein the dosage calculator is derived from a plasma level prediction model that predicts Apixaban drug plasma levels, and the dosage calculator determines the dosage for the patient based in part on the kidney function metric of the patient.

15 Claims, 16 Drawing Sheets

(56) References Cited

OTHER PUBLICATIONS

"Highlights of Prescribing Information", Medication guide, Eliquis (apixaban) tablets for oral use, revised Dec. 2012, 30 pages.

Byon, Wonkyung, et al., "Apixaban: A Clinical Pharmacokinetic and Pharmacodynamic Review", Clinical Pharmacokinetics, vol. 58, 2019, pp. 1265-1279, May 14, 2019, 15 pages.

Cirincione, Brenda, et al., "Population Pharmacokinetics of Apixaban in Subjects With Nonvalvular Atrial Fibrillation", CPT Pharmacometrics Syst. Pharmacol., vol. 7, 2018, pp. 728-738, Sep. 30, 2018, 11 pages.

De Vries, Tim A.C., et al., "Apixaban for Stroke Prevention in Atrial Fibrillation: Why are Event Rates Higher in Clinical Practice than in Randomized Trials?—A Systematic Review", Stroke, Systemic or Venous Thromboembolism, Thrombosis and Haemostasis, vol. 120 No. 9, Jul. 15, 2020, pp. 1323-1329, Jul. 15, 2020, 7 pages.

Frost, Charles, et al., "Apixaban, an oral, direct factor Xa inhibitor: single dose safety, pharmacokinetics, pharmacodynamics and food effect in healthy subjects", British Journal of Clinical Pharmacology, vol. 75 No. 2, Jul. 3, 2012, pp. 476-487, Jul. 3, 2012, 12 pages.

Merli, Geno J, et al., "Apixaban Discontinuation for Invasive or major Surgical procedures (Adios): A prospective cohort study", Vascular Medicine, vol. 27 No. 3, 2022, pp. 269-276, 8 pages.

Raghavan, Nirmala, et al., "Apixaban Metabolism and Pharmacokinetics after Oral Administration to Humans", Drug Metabolism and Disposition, vol. 37 No. 1, 2009, pp. 74-81, 8 pages.

Ueshima, Satoshi, et al., "Population pharmacokinetics and pharmacogenomics of apixaban in Japanese adult patients with atrial fibrillation", British Journal of Clinical Pharmacology, vol. 84, 2018, pp. 1301-1312, 12 pages.

Zadeh, Sadjad Anzabi, et al., "Optimizing warfarin dosing using deep reinforcement learning", Journal of Biomedical Informatics, vol. 137, 2023, 14 pages.

\* cited by examiner

| PID | AGE | sex_num | WEIGHT | ETHN_num | CRCL | DOSE | CYP3A4_inhibitor_int |
|---|---|---|---|---|---|---|---|
| 1003895 | 60 | 1 | 50 | 0 | 120 | 4.5 | 1 |
| 1005788 | 70 | 1 | 50 | 1 | 160 | 3.0 | 0 |
| 1003964 | 60 | 1 | 55 | 0 | 160 | 5.0 | 0 |
| 1005304 | 60 | 0 | 85 | 0 | 120 | 4.0 | 0 |
| 1003647 | 50 | 0 | 105 | 0 | 200 | 3.0 | 1 |

APIXABAN DOSING

FIELD

The present disclosure relates to a method for determining a dosage of Apixaban, a method for generating a dosage calculator and a dosage calculator.

BACKGROUND

The body's clotting system has evolved to a particular equilibrium. This represents a trade-off. Clotting is a protective factor to repair internal blood vessel breakdown or external wounds. However, too much tendency to clot and blood vessels become blocked when this is not desired. This clot can then break off and embolise to distant blood vessels with catastrophic consequences. There is a constant turnover of the multiple molecular components involved in clotting.

Clots can form in any part of the vasculature, in particular the veins of the leg, arteries of the thorax and neck and within the heart. Clots that either embolise from the heart or neck arteries or form directly within the cerebral vasculature can cause a stroke.

Clot is more likely to form in the heart if the heart chambers are enlarged or do not contract normally. Atrial fibrillation (AF), characterized by disorganized atrial electrical activation and contraction in the heart muscle, accounts for ~30% of all hospitalisations for heart rhythm irregularities, occurring in almost 10% of people over the age of 80 with prevalence increasing as the population get older. The clinical consequences of uncontrolled AF results in a 5-fold increase in stroke and blood clots requiring hospitalisation with consequential increasing health costs which in the USA alone is currently estimated to be $8 billion per year.

Management of AF includes methods to restore normal sinus rhythm, control heart rate, and where possible prevent recurrence. When these methods have not succeeded anticoagulants are used to inhibit the formation of the clots. In the past, warfarin has been successfully used, significantly reducing stroke by about 60%, but can lead to severe risks of bleeding due to a narrow therapeutic range, differences in metabolism between individuals, and multiple interactions with a number of co-administered drugs and food stuffs. Warfarin is difficult to prescribe at the correct dose and demands frequent measurements of blood clotting times (international normalised ratio, INR levels) to allow for regular dose adjustment.

Another disease in which anticoagulants are used is in the treatment of thromboembolism where clots are formed in the veins (VTE) and if untreated can lead to disability (pain, scaling ulcers, oedema in the legs), deep vein thrombosis (DVT) and if clots break off can cause pulmonary embolism and death. As many as 600,00 VTEs occur each year in the USA.

New drugs have been developed which allow simplified dose management and have been shown to reduce the chance of developing a major bleeding event when compared to warfarin. These direct acting oral anticoagulants (DOACs) act through different more targeted mechanisms. Whereas warfarin and other similar anticoagulants are indirect inhibitors of Vitamin K through both intrinsic and extrinsic pathways, DOACs work directly on the common pathways lower in the clotting cascade. For example, one DOAC, Apixaban, acts directly by inhibiting the thrombin molecule both in free and bound forms. Thrombin is central to the formation of blood clots. These newer modes of action lead to fewer monitoring requirements, less frequent follow-up, more immediate drug onset and offset effects, particularly important in relating plasma drug levels to activity and fewer drug and food interactions Apixaban is a DOAC licenced for stroke prevention in non-valvular atrial fibrillation, as well as the treatment and prevention of venous thromboembolism; it has been studied in many thousands of patients. The phase III clinical trial ARISTOTLE study [1] has shown that apixaban is superior to warfarin in patients with nonvalvular AF and resulted in similar or lower rates of fatal stroke compared with adjusted-dose of warfarin with the advantage of a small reduction in the risk of intracranial bleeds. The results overall were comparable to those seen in the RELY (Dabigatran) large scale Phase III study (FDA SBA 202155 Medical Review 2012). Apixaban is also used to reduce the tendency to form clots and thus the incidence of stroke in patients from other systemic embolisms.

There are disadvantages to the DOACs such as Apixaban, including lack of efficacy and safety data in patients with severe chronic kidney or hepatic disease, or those with significant valvular disease, lack of easily available monitoring of blood levels and compliance, and higher patient cost in some health care areas. Additionally, whilst reversal agents are now available for some DOACs, they are expensive and do not cover all forms of bleeding.

The limitations in dosage quanta and the prescribing guidelines can result in very limited dosing flexibility for a health care professional (HCP). As a result, patients can be prescribed an inappropriate starting dose and some patients may be excluded from treatment with Apixaban, for example those with kidney impairment. FDA Real World Evidence studies have provided evidence that currently DOACs may be both under dosed leading to an excess of thrombotic events and overdosed, particularly when there is renal impairment, leading to an excess of haemorrhage. This can be a particular issue with Apixaban as there can be a large variability (~6-10 FOLD) in drug plasma levels across the population for a given dose.

The issue of incorrect starting dosage (or even a correct starting dosage) can be further exacerbated by insufficient monitoring. Unlike warfarin, routine monitoring of blood coagulation in patients taking DOACs is not currently recommended, except in certain patients, particularly those with cryptic thromboses, renal failure, the elderly, or those taking certain co-administered drugs. In these latter groups, monitoring is needed but not often undertaken. Recommendations are that such patients should be reviewed at least once per year. This recommendation is often poorly adhered to and often no review is performed at all. Reasons include delegation to general practitioners and general physicians who may be too busy and/or do not have sufficient information and understanding. Furthermore, even when haematology experts give clear instructions to primary care, the instructions are often not followed properly.

A further challenge resulting from insufficient monitoring is managing risk around the times of invasive procedures for an operation such as hip and knee replacements or a lumbar puncture. Management of patients in the perioperative period involves a careful assessment of the relative risk of bleeding or the possibility of a thromboembolic event. Current guidelines are a one size fits all with the result that some patients have their anticoagulation stopped too soon and are thus rendered at high risk of clots, whereas others may have their anticoagulation stopped too late and have higher bleeding risks. As well as risks to the patient, there is also secondary harm from bed blocking from excessive stay in hospital whilst waiting for anticoagulation to wear off. Furthermore, there is also delay in any investigations. For example, an unplanned lumbar puncture which may be required at short notice to diagnose a neurological condition may be delayed for an unnecessarily long period because of concerns around ongoing anticoagulation.

A further area of particular need relates to thrombosis risk in cancer. Management is particularly difficult in cancer because as well as an increased thrombosis risk, there is also an increased bleeding risk. The problems with cancer are increasing with the shift to more home based chemotherapy and thus more chemotherapy lines being inserted, further increasing the thrombosis risk. The requirement for particularly precise control and knowledge of actual risks of haemorrhage would be extremely useful.

The present disclosure provides a method for determining a dosage of Apixaban, a method for generating a dosage calculator and a dosage calculator that may address one or more of the above issues.

SUMMARY

According to a first aspect of the present disclosure there is provided a computer implemented method for determining a dosage of Apixaban for administering to a patient, the method comprising:
  receiving patient data relating to a patient, wherein the patient data includes a kidney function metric;
  processing the patient data with a dosage calculator to determine the dosage of Apixaban for administering to the patient, wherein the dosage calculator is derived from a plasma level prediction model; and
  indicating the dosage.

The patient data may further comprise one or more of: a patient age; a patient ethnicity; a patient sex (or patient gender); a patient weight; a patient genomic type; a patient cardiac metric and a patient medication list.

The patient cardiac metric may comprise an indication that the patient has non-valvular atrial fibrillation.

The patient genomic type may comprise a patient genotype for Pgp transporter genes such as ABCG or metabolic enzymes such as CYP 3A4/5.

The patient medication list may comprise an indication of whether the patient is consuming one or more medications comprising one or more of: a Cytochrome P450 3A4, CYP3A4, inhibitor; a CYP3A4 inducer; a P-glycoprotein (PGP) inhibitor; a PGP inducer; and a drug which increases the risk of bleeding, including a drug with an anticoagulant effect.

The one or more medications may comprise one or more of:
  an additional anticoagulant such as heparin, warfarin, or a direct oral anti-coagulant;
  an antiplatelet such as aspirin, clopidogrel, and ticagrelor;
  a CYP3A4 and/or PGP inhibitor such as itraconazole, ketoconazole, an HIV protease inhibitor, amiodarone, clarithromycin, diltiazem, fluconazole, quinidine, and verapamil;
  a CYP3A4 and/or PGP inducer such as carbamazepine, phenytoin, rifampicin, and St John's Wort; and
  serotonin reuptake inhibitors (such as citalopram), serotonin norepinephrine re-uptake inhibitors (duloxetine), and venlafaxine.

The patient data may further comprise one or more of: reported side-effects; alcohol intake; smoking history, a patient clotting metric; a treatment purpose; patient genetic determinants; patient co-conditions; a patient activity level; a patient dosage compliance; a patient liver function; a patient thrombosis history; a patient haemorrhage history; a patient cancer history; a family thrombosis history; familial stroke history, familial bleeding history; a patient cardiovascular history; a patient metabolic history; a patient blood pressure history; a patient platelet count; a patient heart rate; and a patient haematocrit.

The treatment purpose may comprise: prevention of thrombosis, embolism and/or stroke, optionally including patients with non-valvular atrial fibrillation and one or more risk factors including: a previous stroke or transient ischaemic attach, heart failure, diabetes or hypertension; active thrombosis treatment and/or active pulmonary embolism treatment; prevention of venous thromboembolism in people who have undergone surgery, optionally including hip or knee replacement therapy.

The method may further comprise:
  receiving updated patient data; and
  processing the updated patient data with the dosage calculator to determine an updated dosage; and
  indicating the updated dosage.

The updated patient data may include a patient clotting metric and/or a drug concentration, from a blood test result.

The method may further comprise calibrating the dosage calculator by adjusting the dosage calculator and/or the plasma level prediction model using the patient clotting metric and/or drug concentration.

The plasma level prediction model may comprise a time-based differential equation model for modelling a time dependence of a plasma concentration of Apixaban as a function of the patient data.

Processing the patient data with a dosage calculator to determine the dosage of Apixaban for administering to the patient may comprise:
  receiving a target plasma level metric; and
  calculating the dosage for administering to the patient by processing the patient data and the target plasma level metric with the dosage calculator.

Processing the patient data with a dosage calculator to determine the dosage of Apixaban for administering to the patient may comprise:
  setting an initial value of a dose estimate;
  processing the dose estimate with the dosage calculator to estimate a plasma level metric;
  comparing the plasma level metric to a target plasma level metric; and
  determining the dosage for administering to the patient by refining the dose estimate based on the comparison.

Refining the dose estimate may comprise:
  iteratively adjusting the dose estimate and recalculating the plasma level metric until a difference between the estimated plasma level metric and the target plasma level metric is less than a difference threshold; or
  setting one or more further values of the dose estimate and processing the one or more further values with the dosage calculator to estimate one or more further plasma level metrics; and
  determining the dosage for administering to the patient by interpolating the dosage value corresponding to the target plasma level metric based on the relationship between the initial value of the dose estimate, the one or more further values of the dose estimate, the plasma level metric and the one or more further plasma level metrics.

The target plasma level metric may comprise one or more of:
- a target trough plasma level comprising an ideal therapeutic level;
  - a target maximum plasma level being less than a maximum level threshold;
  - a target average plasma level over a dosing interval at steady state comprising an ideal therapeutic level;
  - a target area under the curve of a plasma level time profile comprising an ideal therapeutic level;
  - a target ratio of a maximum plasma level to a trough plasma level comprising an ideal therapeutic ratio and level; or
  - a target ratio of the maximum plasma level to the area under the curve of the plasma level time profile comprising an ideal therapeutic ratio and level.

The patient data may comprise one or more target dependent patient parameters comprising: reported side effects; a patient thrombosis history; a patient haemorrhage history; a patient cancer history; a patient stroke history; a patient liver function metric; a patient heart function metric; a patient brain state; a patient smoking history; a patient alcohol history; a patient blood pressure; a patient activity level; a patient dosage compliance; a patient mobility state; a patient menstruation state; a patient inflammation state; a patient infection state; a patient co-medication; a patient co-condition; a blood clotting metric; a patient genetic profile; familial stroke history, familial bleeding history; familial hypertension history; a patient cardiovascular history; a patient metabolic history; a patient blood pressure history; a patient blood pressure; a patient heart rate, a patient platelet count; a patient haematocrit; and a patient hydration state, wherein the method comprises:
- determining the target plasma level metric as a personalised target plasma level metric based on the one or more target dependent patient parameters.

The method may comprise:
- determining a bleeding risk score for the patient based on one or more of the target dependent patient parameters; and
- determining a thrombosis risk score for the patient based on one or more of the target dependent patient parameters; and
- determining the personalised target plasma level metric based on the bleeding risk score and/or the thrombosis risk score.

The method may comprise:
- determining a bleeding risk score for the patient based on one or more of:
  - a time since one or more bleeding risk events, wherein the bleeding risk events comprise any of: an injury; a surgical procedure; needle penetration; or a patient fall, as indicated by the patient haemorrhage history;
  - a severity of the clotting risk event;
  - an age of the patient;
  - the patient cancer history;
  - the patient blood pressure;
  - the patient liver function metric;
  - a time since a haemorrhagic stroke as indicated by the patient stroke history;
  - an extent of amyloid in the patient's brain as indicated by the patient brain state;
  - the blood clotting metric;
  - an indication of aspirin, clopidogrel, NSAIDS, steroids or antidepressants as indicated by the patient co-medication;
  - alcohol consumption as indicated by the patient alcohol history; and/or
- determining a thrombosis risk score for the patient based on one or more of:
  - a time since one or more clotting risk events, wherein the clotting risk events comprise any of:
  - a thrombosis; an injury; a surgical procedure; needle penetration; or a patient fall as indicated by the patient thrombosis history;
  - an episode of atrial fibrillation as indicated by the patient heart function metric;
  - an episode of chemotherapy as indicated by the patient cancer history;
  - a severity of the clotting risk event;
  - the patient cancer history;
  - the patient blood pressure;
  - the patient mobility;
    - the patient blood pressure;
    - the blood clotting metric;
    - the patient genetic profile;
    - the time since an ischemic stroke as indicated by the patient stroke history;
    - the patient menstruation state;
    - an indication of oral contraceptive as indicated by the patient co-medication; and
    - the patient hydration state,
  wherein determining the personalised target plasma level metric is determined based on the bleeding risk score and/or the thrombosis risk score.

The personalised target plasma level metric may comprise:
- a trough plasma level comprising a personalised adjustment to an ideal therapeutic level based on the one or more target dependent patient parameters; and/or
- a ratio of a maximum plasma level to an area under a plasma level time profile being less than a bleeding risk threshold.

The ideal therapeutic level may comprise:
- a trough plasma level range of 34 to 100 ng/ml and may comprise a trough plasma level range of 50-84 ng/ml;
- an average plasma level over 24 hours of 40-150 ng/ml and may comprise an average plasma level of 80-110 ng/ml and may comprise an average plasma level of 95 ng/ml.

The method may comprise:
- processing the patient data with the dosage calculator to determine a plasma level metric; and
- indicating one or more of:
  - the plasma level metric;
  - a patient thrombosis risk based on the plasma level metric; or
  - a patient haemorrhage risk based on the plasma level metric.

The plasma level metric may comprise a plasma level time profile.

Indicating one or more of: the plasma level metric; the patient thrombosis risk; or the patient haemorrhage risk, may comprise indicating to the patient or a health care professional. Indicating may be via a user interface.

The patient data may comprises one or more dosage times at which the patient received a dose of Apixaban. The plasma level metric may comprise a time-dependent plasma level metric based on the one or more dosage times.

The plasma level metric may comprise one or more of:
- a plasma level time profile;
- a maximum plasma level;
- a trough plasma level;

an average plasma level over a dosing interval at steady state;

an area under the curve of the plasma level time profile;

a ratio of the maximum plasma level to the trough plasma level; or a ratio of the maximum plasma level to the area under the curve of the plasma level time profile.

The dosage calculator may comprise a machine learning algorithm trained using the plasma level prediction model.

The dosage calculator may comprise a machine learning algorithm trained using simulated population data obtained from the plasma level prediction model.

The dosage calculator may comprise a machine learning algorithm trained using:

simulated population data obtained from the plasma level prediction model; and real population data.

The machine learning algorithm may be locked to prevent further adjustment to the machine learning algorithm.

The machine learning algorithm may comprise an adjustable machine learning algorithm. The method may further comprise:

receiving updated patient data including a patient clotting metric from a blood test result; and adjusting the machine learning model based on the patient clotting metric.

The dosage calculator may comprise the plasma level prediction model.

The dosage calculator may comprise one or more look-up tables defined according to simulated population data obtained from the plasma level prediction model.

Processing the patient data with the dosage calculator to determine the dosage of Apixaban for administering to the patient may comprise:

processing the patient data with the dosage calculator to determine an ideal dosage regime; and selecting the dosage for administering to the patient from a selection of available dosage regimes based on the ideal dosage regime.

The selection of available dosage regimes may comprise dosage amounts comprising: 2.5 or 5 mg BID of Apixaban.

The selection of available dosage regimes may comprise dosage amounts comprising:

any multiple of 0.1 mg; or any multiple of 1 mg.

The selection of available dosage regimes may comprise selection of a microgranular or liquid formulation for titrating an ideal dosage amount of the ideal dosage regimen.

Processing the patient data with the dosage calculator to determine the dosage of Apixaban for administering to the patient may comprise processing the patient data with the dosage calculator to determine one or more of: a dosage amount; a dosage time; a dosage frequency; and/or a dosage type.

The dosage type may comprise a Apixaban slow-release formulation with a specific release time.

The specific release time may be at least 6 hours, for example at least 12 hours. In this way, a single dose would cover 24 hours.

Indicating the dosage may comprise indicating the dosage to a health care professional and/or to the patient.

Indicating the dosage may comprise indicating the dosage to a health care professional and/or the patient via a user interface. The user interface may comprise a digital app. the method may comprise performing one or more of the steps within the digital app.

Any method disclosed herein for use in stroke prevention, thrombosis treatment, blood clot prevention or dosage management for an invasive procedure on the patient.

The patient may be a cancer patient.

According to a second aspect of the present disclosure there is provided a computer readable medium comprising instructions which, when executed by one or more processors, cause the one or more processors to carry out any method disclosed herein.

According to a third aspect of the present disclosure, there is provided a method of generating a dosage calculator for determining a dosage of Apixaban for administering to a patient, the method comprising:

receiving simulated population data calculated using a plasma level prediction model; and training a machine learning dosage calculator using the simulated population data.

The simulated population data may comprise simulated population data for at least 100,000 simulated patients.

The simulated population data may comprise simulated patient data, simulated dosages and/or simulated plasma level metrics.

The method may comprise calculating the simulated population data using the plasma level prediction model.

Calculating simulated population data using a plasma level prediction model may comprise:

defining simulated patient data for a patient population comprising a plurality of simulated patients and a corresponding plurality of simulated dosages; and calculating plasma level metrics for each of the plurality of simulated patients by processing the simulated dosages and simulated patient data using the plasma level prediction model to determine simulated plasma level metrics;

determining the simulated population data comprising the simulated patient data, the simulated dosages and the simulated plasma level metrics.

The simulated patient data may comprise one or more of: a kidney function metric; a patient age; a patient ethnicity; a patient gender; a patient weight; a patient genomic type; a patient cardiac metric and a patient medication list.

Defining the simulated patient data may comprise: receiving a population distribution for each parameter type of the simulated patient data; and generating each simulated patient by probabilistic selection of each parameter type according to the respective population distribution. Defining the simulated patient data may comprise: defining a plurality of discrete values for each parameter type; and generating each simulated patient data as a different combinations of one discrete value from each parameter type. Generating each simulated patient may comprise generating simulated patient data for every possible combination of one discrete value from each parameter type.

The plasma level prediction model may comprise a time-based differential equation model for modelling a time dependence of a plasma concentration of Apixaban as a function of the patient data.

The plasma level prediction model may comprise a compartment model for modelling a time dependence of a plasma concentration of Apixaban as a function of the patient data.

Training the machine learning dosage calculator may comprise training the machine learning dosage calculator using the simulated population data and real patient data.

The method may comprise validating the machine learning model using further simulated population data. The further simulated population data may be different to the simulated population data.

The method may comprise locking the machine learning dosage calculator to prevent further adjustment to the machine learning dosage calculator.

The method may further comprise calibrating the machine learning algorithm for a patient based on a measured drug plasma level or coagulation measure obtained from a blood test on the patient.

The machine learning dosage calculator may be configured to directly calculate the dosage for administering to the patient by processing patient data and a target plasma level metric.

The patient data may comprise one or more of: a kidney function metric; a patient age; a patient ethnicity; a patient gender; a patient weight; a patient haemoglobin level; a patient left ventricular function; and a patient medication list.

According to a fourth aspect of the present disclosure there is provided a dosage calculator for determining a dosage of Apixaban for administering to a patient, the dosage calculator comprising one or more processors configured to:
receive patient data relating to a patient, wherein the patient data includes a kidney function metric;
process the patient data with a dosage calculator to determine the dosage of Apixaban for administering to the patient, wherein the dosage calculator is derived from a plasma level prediction model; and
indicate the dosage.

According to a fifth aspect of the present disclosure there is provided a computer implemented method for determining a procedure wait time for a patient following withdrawal of a direct oral anti-coagulant, DOAC, in advance of an invasive procedure, the method comprising:
receiving patient data relating to a patient, wherein the patient data includes a kidney function metric and a DOAC dosage;
processing the patient data with a dosage calculator to determine the procedure wait time for a drug plasma level to fall below an invasive procedure plasma level threshold, wherein the dosage calculator is derived from a plasma level prediction model; and
indicating the procedure wait time.

The DOAC may comprise Apixaban or Dabigatran.

The method may comprise administering the procedure wait time in advance of the invasive procedure to reduce a risk of haemorrhage during the invasive procedure.

The patient data may further comprise one or more of: a patient age; a patient ethnicity; a patient sex (or patient gender); a patient weight; a patient genomic type; a patient cardiac metric and a patient medication list.

The patient cardiac metric may comprise an indication that the patient has non-valvular atrial fibrillation.

The patient genomic type may comprise a patient genotype for Pgp transporter genes such as ABCG or metabolic enzymes such as CYP 3A4/5.

The patient medication list may comprise an indication of whether the patient is consuming one or more medications comprising one or more of: a Cytochrome P450 3A4, CYP3A4, inhibitor; a CYP3A4 inducer; a P-glycoprotein (PGP) inhibitor; a PGP inducer; and a drug which increases the risk of bleeding, including a drug with an anticoagulant effect.

The one or more medications may comprise one or more of:
an additional anticoagulant such as heparin, warfarin, or a direct oral anti-coagulant;
an antiplatelet such as aspirin, clopidogrel, and ticagrelor;
a CYP3A4 and/or PGP inhibitor such as itraconazole, ketoconazole, an HIV protease inhibitor, amiodarone, clarithromycin, diltiazem, fluconazole, quinidine, and verapamil;
a CYP3A4 and/or PGP inducer such as carbamazepine, phenytoin, rifampicin, and St John's Wort; and
serotonin reuptake inhibitors (such as citalopram), serotonin norepinephrine re-uptake inhibitors (duloxetine), and venlafaxine.

According to a sixth aspect of the present disclosure, there is provided a method for administering a dosage of Apixaban to a patient for the treatment or prevention of thrombosis, the method comprising:
administering a dosage of Apixaban to the patient, wherein the dosage of apixaban is determined by:
receiving patient data relating to a patient, wherein the patient data includes a kidney function metric of the patient; and
processing, using one or more processors, the patient data with a dosage calculator to determine the dosage of Apixaban for the patient, wherein the dosage calculator is derived from a plasma level prediction model that predicts Apixaban drug plasma levels, and the dosage calculator determines the dosage for the patient based in part on the kidney function metric of the patient.

According to a seventh aspect of the present disclosure there is provided apixaban for use in the treatment of stroke prevention, thrombosis treatment or blood clot prevention, wherein the apixaban dosage is determined by steps comprising:
receiving patient data relating to a patient, wherein the patient data includes a kidney function metric;
processing the patient data with a dosage calculator to determine the dosage of Apixaban for administering to the patient, wherein the dosage calculator is derived from a plasma level prediction model; and
indicating the dosage.

According to an eighth aspect of the present disclosure there is provided a method of treating thrombosis, stroke prevention or blood clot prevention comprising administering apixaban to a patient in need thereof, wherein the apixaban dosage is determined by the steps comprising:
receiving patient data relating to a patient, wherein the patient data includes a kidney function metric;
processing the patient data with a dosage calculator to determine the dosage of Apixaban for administering to the patient, wherein the dosage calculator is derived from a plasma level prediction model; and
indicating the dosage.

The patient data may comprise one or more of: a patient age; a patient ethnicity; a patient gender; a patient weight; a patient haemoglobin level; a patient cardiac metric; and a patient medication list.

There may be provided a computer program, which when run on a computer, causes the computer to configure any apparatus, including a circuit, controller, converter, or device disclosed herein or perform any method disclosed herein. The computer program may be a software implementation, and the computer may be considered as any appropriate hardware, including a digital signal processor, a microcontroller, and an implementation in read only memory (ROM), erasable programmable read only memory (EPROM) or electronically erasable programmable read only memory (EEPROM), as non-limiting examples. The software may be an assembly program.

The computer program may be provided on a computer readable medium, which may be a physical computer readable medium such as a disc or a memory device, or may be embodied as a transient signal. Such a transient signal may be a network download, including an internet download. There may be provided one or more non-transitory computer-readable storage media storing computer-executable instructions that, when executed by a computing system, causes the computing system to perform any method disclosed herein.

BRIEF DESCRIPTION OF THE DRAWINGS

One or more embodiments will now be described by way of example only with reference to the accompanying drawings in which.

DETAILED DESCRIPTION

Apixaban Pharmacokinetics (Pk)—Plasma Level Variability

Figure 1:
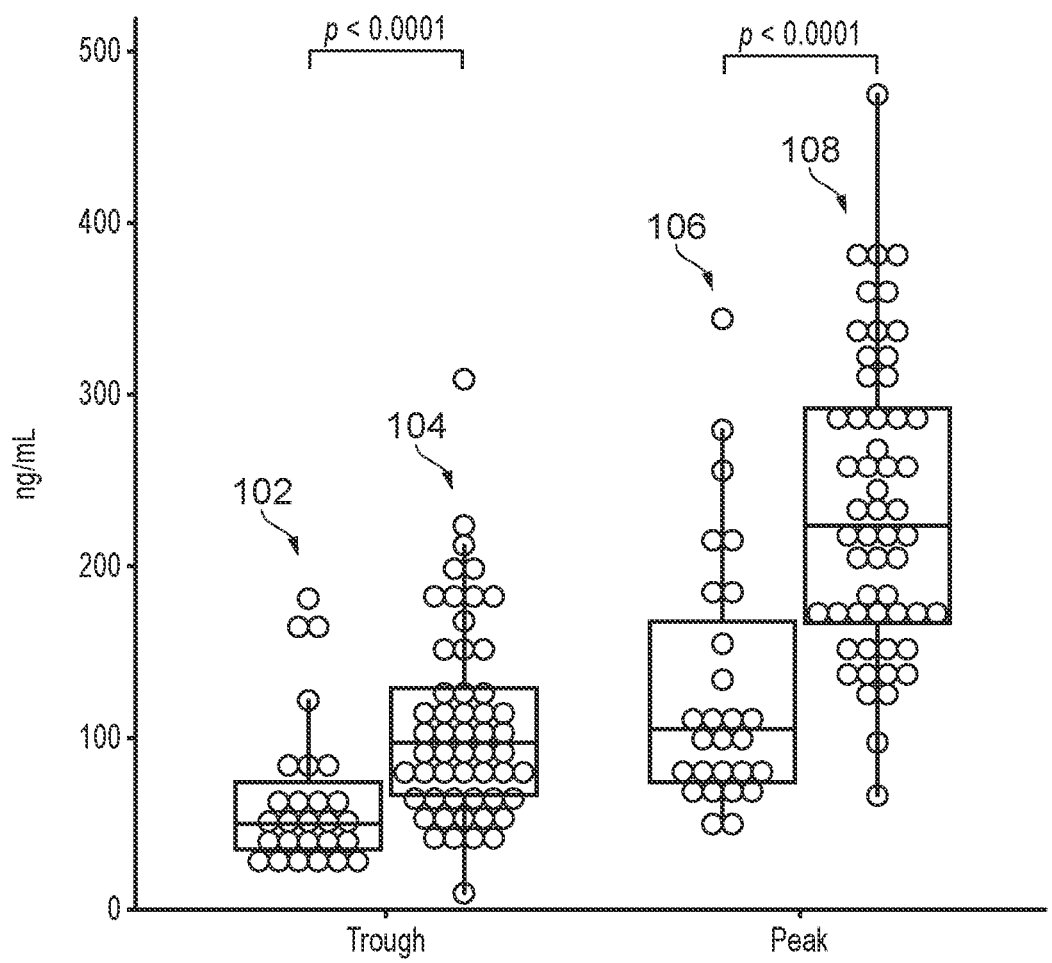
FIG. 1 illustrates a variation in Apixaban plasma levels across a patient population.

Absorption of Apixaban is relatively slow, with maximum concentration not occurring until 3-4 hours after oral administration (range 1-6 hours) and this is delayed by ~1 hour with food (range 1-9 hours) although total exposure is unaffected. The absolute oral bioavailability is ~50% due to some first pass metabolism but also incomplete absorption [2].

Plasma exposure increases proportionally with dose up to 10 mg. Above this dose absorption is less than proportional due to its dissolution limited bioavailability. Total body clearance is low (50 ml/min~3% liver blood flow) but the volume of distribution is small (0.3 L/kg). The apparent oral half-life with tablets is intermediate (~12 h) necessitating twice a day dosing. This apparent half-life is less than that seen after iv or oral solution ~5 hours suggesting that absorption is rate limited in tablet form [3,4]. After repeated administration steady state occurs by 3 days with ~65% increase in levels compared to the first dose.

Elimination occurs via several routes including metabolism (~20%), biliary excretion, and direct intestinal excretion into the faeces (34% unchanged drug), which accounts for the relatively low absorption of the drug. Renal clearance on the other hand is low (15 ml/min~12% of GFR) with only ~20-25% of the dose excreted by this route [4], whereas for the DOAC dabigatran, ~80% is cleared through the kidneys.

Metabolism mainly occurs by Cytochrome P450 3A4 (CYP 3A4) which can lead to a variability in first pass metabolism and plasma levels in subjects (Coefficient of variance in healthy human volunteers (CV in HHV)) for maximum plasma concentration, Cmax, and area-under-the-curve (AUC) of the plasma level time profile is ~30%) [3]. There are no active metabolites in plasma.

From in vitro studies the drug does not inhibit or induce metabolic enzymes or transport mechanisms. However, Apixaban is a substrate primarily for CYP3A4 which is linked with P-glycoprotein (PgP) transporter. Ketoconazole (CYP 3A4 inhibitor) can increase exposure (drug levels) ~2 fold and rifampicin (a PgP inhibitor) can decrease exposure by ~50%. The situation is made more complex when drugs with both activities are co-administered For example, Clarithromycin, an inhibitor of P-gp and a strong inhibitor of CYP3A4, led to a 1.3- and 1.6-fold increase in mean apixaban Cmax and AUC 0-∞, respectively [2]. The manufacturer of Apixaban recommends avoiding concurrent use of Apixaban with some strong inhibitors of these mechanisms, such as itraconazole, ketoconazole, and HIV protease inhibitors.

Previous studies [2] have shown that patients with low body weight (≤50 kg) had approximately 27% and 20% higher maximum apixaban plasma concentration (Cmax) and area under the curve plasma concentration (AUC0-∞), respectively, compared with the reference body weight group (65-85 kg). Conversely, patients with a high body weight (≥120 kg) had approximately 31% and 23% lower apixaban Cmax and AUC0-∞, respectively, compared with the reference group.

Posology

There are 2 doses of Apixaban available in Europe and the USA (2.5 and 5 mg) to be taken twice a day. However the posology is different in the 2 countries:

The FDA recommended dose is 5 mg orally twice daily. In patients with at least 2 of the following characteristics: age≥80 years, body weight≤60 kg, or serum creatinine≥1.5 mg/dl, the recommended dose is 2.5 mg orally twice daily [5]

MHRA dose information is more complex [6]:
  Prophylaxis of stroke and systemic embolism in non-valvular atrial fibrillation and at least one risk factor (such as previous stroke or transient ischaemic attack, symptomatic heart failure, diabetes mellitus, hypertension, or age 75 years and over):
    5 mg BID; or
    Alternatively 2.5 BID, reduced dose used in patients with at least two of the following characteristics: age 80 years and over, body-weight 60 kg or less, or serum creatinine 133 micromol/litre and over.
  Prophylaxis of venous thromboembolism following knee replacement
    2.5 mg BID for 10-14 days, to be started 12-24 hours after surgery.
  Prophylaxis of venous thromboembolism following hip replacement
    2.5 mg BID for 32-38 days, to be started 12-24 hours after surgery.
  Treatment of deep-vein thrombosis, Treatment of pulmonary embolism
    Initially 10 mg BID for 7 days, then maintenance 5 mg BID.
  Prophylaxis of recurrent deep-vein thrombosis, Prophylaxis of recurrent pulmonary embolism
    2.5 mg BID following completion of 6 months anticoagulant treatment.
  Preventing Clots in legs and lungs
    Initially 10 mg BID for 7 days then 5 mg BID.

However there is still large inter-subject variability in the resulting measures of coagulation and outcomes between underdosed (increased morbidity and mortality) and overdosed (increased haemorrhagic incidences and GI disturbances).

Several studies have shown relationships between plasma drug levels and clinical outcome, suggesting that trough levels between 50-75 ng/ml and/or daily average levels of ~125 ng/ml provide the best balance between reduction in stroke and minimization of bleeding. A trough level is the plasma level before a next scheduled dose (typically the morning dose). However, measuring drug levels in general practice is costly and is infrequently undertaken. There appears to be relationships between drug levels and particular measures of the activity of Apixaban on coagulation, namely prothrombin Time (aPT), modified prothrombin time (mPT) and anti factor Xa and these could form a way of monitoring patient outcomes.

In summary, a large variability in drug plasma levels between patients is driven by: the influence of renal function; body weight, the effect of other drugs; low absorption; and other factors (discussed further below). FIG. 1 (taken from [7]) illustrates the variation of steady state Apixaban plasma levels across a population for 2.5 mg and 5.0 mg doses. The Figure illustrates a first range of trough plasma levels 102 for patients administered 2.5 mg, a second range of trough plasma levels 104 for patients administered 5.0 mg, a first range of maximum plasma levels 106 for patients administered 2.5 mg and a second range of maximum plasma levels 108 for patients administered 5.0 mg.

It can be seen that there is a very large range of both peak and trough plasma levels from the two doses used in the study. For the 2.5 mg dose the trough plasma level ranged from ~20-180 ng/ml whilst for the 5 mg dose the range was ~ 10-310 ng/ml whilst the range for peak levels was even greater. This illustrates the large inter-subject differences in absorption and clearance of the drug from the body due to the factors listed above and described herein.

Overview of the Invention

The present disclosure provides a method for determining a dosage of Apixaban for administering to a patient that utilizes a dosage calculator derived from a plasma level prediction model. The method may determine the dosage without requiring plasma drug level measurements. The dosage calculator can process patient data including a kidney function metric to indicate a dosage for administering to the patient.

Figure 2:
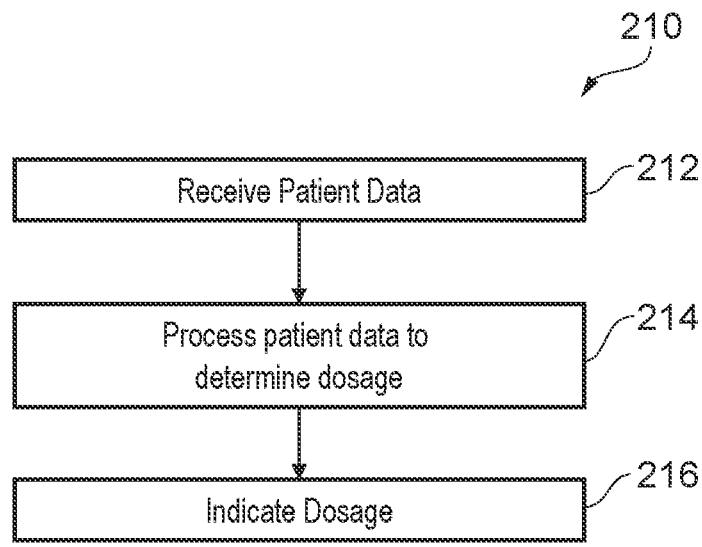
FIG. 2 illustrates a method for determining a dosage of Apixaban for administering to the patient according to an embodiment of the present disclosure.

FIG. 2 illustrates a method 210 for determining a dosage of Apixaban for administering to the patient according to an embodiment of the present disclosure.

A first step 212 comprises receiving patient data relating to a patient. The patient data includes a kidney function metric, which may be a measured creatinine clearance. In some examples the kidney function metric may comprise other renal function metrics such as Inulin cystatin C, beta trace proteins, 51Cr-EDTA (radioactive chromium complexed with ethylene diamine tetracetic acid), 99Tc-EDTA (radioactive technetium complexed with ethylene diamine tetracetic acid). As described above and below, kidney function is a significant driver of Apixaban drug plasma level variability between patients.

A second step 214 comprises processing the patient data with a dosage calculator to determine the dosage of Apixaban for administering to the patient. The dosage calculator is derived from a plasma level prediction model. Example dosage calculators and plasma level prediction models are discussed in detail below.

A third step 216 comprises indicating the dosage.

The method advantageously accounts for one of the biggest drivers of variability in Apixaban drug plasma levels-kidney function. Large variation can arise particularly when renal clearance is high (>150 ml/min) or low (<80 ml/min).

The term Apixaban drug plasma level may also be referred to herein as Apixaban blood plasma level, blood plasma level, drug plasma level or simply plasma level. The term level may be referred to as a concentration. As described below, embodiments of the method can process patient data comprising a plurality of parameters that contribute to plasma level variability, such as demographic data, medication data and patient condition data, to advantageously provide more accurate dosages for patients. The method can calculate a starting dose for a patient. The method can also continue to monitor patient data and provide a revised dose for a patient as their patient data changes. In this way, the method can address the provision of inaccurate starting doses and the lack of ongoing monitoring for DOACs described above. As described below, the method may indicate dosage amounts that differ from the standard dosages available. In some embodiments, the method may recommend novel dosage amounts provided by novel dosage forms including liquid or microgranule formulations or other known solubility enhancement formulations. As mentioned above, microgranules may improve absorption which may reduce inter-subject variability in drug plasma levels. This can advantageously make Apixaban available for patients for which the drug is currently contra-indicated and provide precision dosing for patients in which achieving the correct plasma level is critical (e.g. cancer patients). As described below, the method can also encompass personalisation by providing personalised target plasma metrics on an individual basis based on the patient data.

Plasma Level Prediction Model

In relation to the second step 214, the plasma level prediction model may comprise a theoretical model that can predict a Apixaban drug plasma level based on a dosage and the patient data. In some examples, the plasma level prediction model may be a time-dependent differential equation based (or rate equation based) model. The plasma level prediction model may comprise a compartment model such as a two-compartment model, or any other PKPD analytical model for predicting the drug plasma level as a function of patient data.

Figure 3:
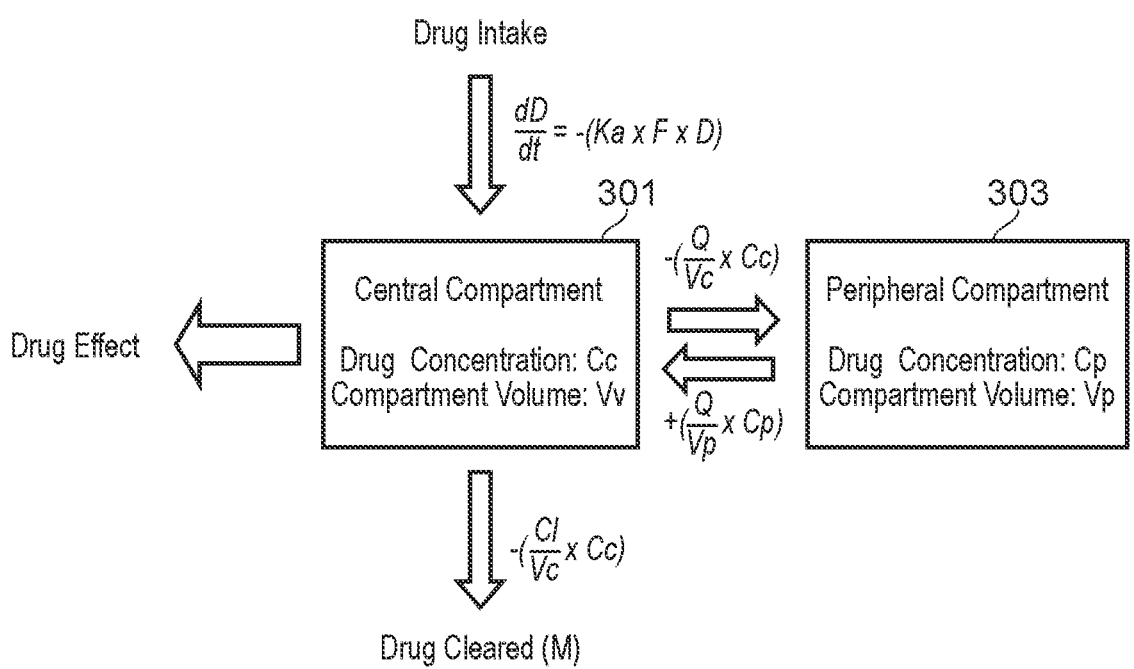
FIG. 3 illustrates an example two-compartment model that may provide the plasma level prediction model according to one or more embodiments.

FIG. 3 illustrates an example two-compartment model that may provide the plasma level prediction model according to one or more embodiments. A central compartment 301 may represent a target location in the body in which the drug provides a therapeutic effect. In the example of Apixaban, the central compartment 301 represents the blood or plasma, however the central compartment 301 may comprise other locations (e.g. liver, tissue, etc) for other drugs. The central compartment 301 has a central compartment drug concentration, Cc, (the drug plasma level in this example) and a central compartment volume, Vc. Drug intake to the central compartment 301 from the administered drug may be defined by:

$$\frac{dD}{dt} = -(Ka \times F \times D) \quad \text{(Eq 1)}$$

where Ka is a first order drug absorption rate constant: F is a relative bioavailability of the drug; and D is the drug dosage.

Drug clearance from the central compartment 301, for example via the kidneys, may be defined as:

$$\frac{dM}{dt} = +\left(\frac{CL}{Vc} \times Cc\right) \quad \text{(Eq 2)}$$

where M is the drug (mass) cleared from central compartment and CL is the total body clearance of the drug from the central compartment.

A peripheral compartment 303 may represent locations in the body in which the drug may reside and not necessarily provide a therapeutic effect. The peripheral compartment 303 has a peripheral compartment drug concentration, Cp, and a peripheral compartment volume, Vp. A rate of change of the peripheral compartment drug concentration, Cp, resulting from the flow of drug between the two compartments may be defined as:

$$\frac{dCp}{dt} = +\left(\frac{Q}{Vc} \times Cc\right) - \left(\frac{Q}{Vp} \times Cp\right) \quad \text{(Eq 3)}$$

where Q is an intercompartmental clearance between the central and peripheral compartments.

Combining everything together, the rate of change of the central compartment drug concentration, Cc, can be written as:

$$\frac{dCc}{dt} = +\left(\frac{Ka}{Vc} \times F \times D\right) - \left(\frac{Cl}{Vc} \times Cc\right) - \left(\frac{Q}{Vc} \times Cc\right) + \left(\frac{Q}{Vp} \times Cp\right) \quad \text{(Eq 4)}$$

Estimated values of the specific parameters, and estimated functions of the specific variables, for the model can be obtained from a patient study. For example, previous studies [2,8] have used a two compartmental model for Apixaban. According to an embodiment of the present disclosure there is provided a plasma level prediction model that was developed based on previous studies. The model uses a linear two compartment model parameterized in terms of apparent oral clearance (CL/F; L/hr), apparent inter-compartmental clearance (Q/F; L/hr), apparent volume of distribution (central [V c/F], and peripheral [V p/F]; L), and first-order absorption rate constant (Ka; hr$^{-1}$).

In this example, total apixaban clearance is split into renal ($CL_R$) and non-renal ($CL_{NR}$) elimination components. The effect of renal function (creatinine clearance (CrCL): can be calculated with the Cockcroft-Gault equation using an upper limit of 150 mL/min. The base model was for a male individual of 60 yrs, 85 kg and CrCl=100 ml/min:

$$\frac{CL_i}{F}(\text{base}) = \left\{\frac{CL_{NR}}{F} + \frac{CL_R}{F} \cdot \left[\frac{CrCL_i}{CrCL_{ref}}\right]^{\theta_1} \cdot (1 - \text{FLAG}) + \frac{CL_R}{F} \cdot \left[\frac{150}{CrCL_{ref}}\right]^{\theta_2} \cdot \text{FLAG}\right\} e^{\eta_i} \quad \text{(Eq 5)}$$

where $CL_i/F$ is apixaban apparent plasma clearance for individual i, $CL_{NR}/F$ is the non-renal component of $CL_i/F$, $CL_R/F$ is the renal component of $CL_i/F$, $CrCL_i$ is the creatinine clearance for individual i, $CrCL_{ref}$ is the reference value of 100 mL/min, $\theta_1$ and $\theta_2$ are the power coefficients for the relationship between $CrCL_i$ and Cli/F, FLAG is an indicator variable which is 1 when $CrCL_i$ is >150 mL/min and zero otherwise, and ηi is the random effect for individual i.

In this example, non-renal clearance is adjusted as a function of age and/or sex:

$$\frac{CL_{NR}}{F}(Age, Sex) = \frac{CL_{NR}}{F}(Ref) * \theta_{AGE} * \theta_{SEX} \quad (Eq\ 6)$$

$$\theta_{AGE} = 1.0 + AGE_P * \frac{(AGE - AGE_{ref})}{AGE_{ref}} \quad (Eq\ 7)$$

In this example, total clearance is adjusted as a function of ethnicity and/or CYP3A4 inhibitors:

$$\frac{CL_i}{F}(Ethn, CYP3A4) = \frac{CL_i}{F}(base) * \theta_{Ethn} * \theta_{CYP3A4} \quad (Eq\ 8)$$

In some examples, the total clearance may also be reduced by an AF reduction factor for patients with non-valvular atrial fibrillation. In some examples, the AF reduction factor may be between 10-20%, for example 14%.

In this example, the central compartment volume, Vc/F is modified by patient weight:

$$\theta_{WT} = 1.0 + WT_P * \frac{(WT - WT_{ref})}{WT} \quad (Eq\ 9)$$

In this example, a function for relative bioavailability F is included based on the non-linear absorption of doses above 2.5 mg using a simplified power model:

$$F = 1.0 \quad \text{for dose} \le 2.5\ mg \quad (Eq\ 10)$$

$$F = 1 - I_{50}\left[\frac{(Dose - 2.5)}{47.5}\right]^{\gamma} \quad \text{for dose} > 2.5\ mg$$

$$I_{50} = \frac{e^{\theta_9}}{1 + e^{\theta_9}} \quad (Eq\ 11)$$

where F is the relative bioavailability of a given Dose greater than 2.5 mg, Iso is the decrease in relative bioavailability for a 50-mg apixaban dose and $\gamma$ is the shape parameter that controls the relationship between dose and F.

Values of specific parameters of equations 1 to 11 are included in table 1 and values may also be found in previous studies. The absorption rate may include a morning absorption rate and an evening absorption rate. Observed drug plasma levels are ~50% lower in the evening than in the morning. The reasons for this are not clear and may be due to poor patient compliance for evening dosing or that evening dosages are administered with food.

TABLE 1

Specific parameter values of model

| Parameter | Value |
| --- | --- |
| Absorption Rate Ka (1/hr) | 0.440 morning dose 0.239 evening dose |

TABLE 1-continued

Specific parameter values of model

| Parameter | Value |
| --- | --- |
| Clearances | |
| $CL_R/F$ (L/hr) | 1.83 |
| $CL_{NR}/F$ (Ref) (L/hr) | 2.52 |
| $CrCL_{ref}$ | 100 |
| $AGE_P$ | 0.267 |
| $AGE_{REF}$ (years) | 60 |
| $\theta_{SEX}$ | 1.0-0.223 for female |
| $\theta_{Ethn}$ | 1.0-0.168 for Asian |
| $\theta_{CYP3A4}$ | 1.0-0.203 |
| $WT_P$ | 0.523 |
| $WT_{ref}$ (kg) | 85.0 |
| $V_C/F$ | 32.1 |
| $Q/F$ | 1.62 |
| $V_P/F$ | 19.8 |
| $\Gamma$ | 0.853 |
| $\theta_9$ | −0.321 |
| $\theta_1, \theta_2$ | 1.0 |

Table 2 summarises the change in drug level exposure resulting from different covariates of the model.

TABLE 2

Change in drug level exposure

| Covariate | Change in Drug Level Exposure (AUC) or activity |
| --- | --- |
| Absorption Rate | 48% slower absorption when administered in evening relative to administration at other times in the day |
| Renal clearance CLR/Fa (L/hr) | VTE treatment subjects with mild (CrCL of 65 mL/min), moderate (CrCL of 40 mL/min), and severe (CrCL of 15 mL/min) renal impairment would have approximately 35%, 60%, and 85% lower $CL_R/F$, respectively, than a reference VTE treatment subject with normal renal function (CrCL of 100 mL/min) |
| Sex | ~13% reduction in CL/F in females compared to males, assuming no change in $CL_R/F$ |
| Asian | ~17% reduction in CL/F in Asians compared to other ethnicities |
| Weight | 24% reduction in $V_C/F$ for a 50-kg subject and a 20% increase for a 120-kg subject relative to the reference subject with a body weight of 85 kg |
| CYP3A4/PgP inhibitors | ~20% decrease in Cl/F |
| Ketaconazole [a] | ~100% increase in AUC |
| Diltiazem | ~40% increase in AUC |
| Clarithromycin | ~50% increase in Cmax and AUC |
| Riampin [b] | ~50% decrease in AUC |

[a] Or other CYP 3A4/PgP inhibitors such as antifungals itraconazole, or ritonavir
[b] Or other CYP 3A4 inducers carbamazepine, phenytoin, St Johns Wort In some examples, the plasma level prediction model may include fewer or more than the covariate adjustments described above. In some examples, the model may include adjustments for the effects of PgP transporter (ABCG2) and metabolic enzyme genes (CYP3A5). A previous study [9] found 1.49 and 1.52 times higher plasma levels respectively in those with genomic subtypes. Their final model included the adjustment:

$$\frac{CL}{F} = 1.53 \cdot \left\{\left(\frac{CCR}{70}\right)^{0.7} + 0.312^{CYP3A5} \cdot 0.341^{ABCG2}\right\} \quad (Eq\ 12)$$

where the dichotomous parameter CYP3A5 is equal to 1 if patients had the CYP3A5*1/*3 or *3/*3 genotype, otherwise it was set to 0, and the dichotomous parameter ABCG2 is equal to 1 if patients had the ABCG2 421A/A genotype, otherwise it was set to 0.

According to one or more embodiments of the present disclosure, a two-compartment plasma level prediction model may be defined by equations 1 to 4 with expressions for Cl, Vc and F adjusted according to equations 5 to 11, with parameter estimates taken from Table 1.

FIGS. 4A to 4D illustrate comparison and validation of the above disclosed model with published experimental data from clinical trials. In general, for each plot showing variation of a variable, other variables are set to population averages for the underlying study data unless otherwise stated.

Figure 4A:
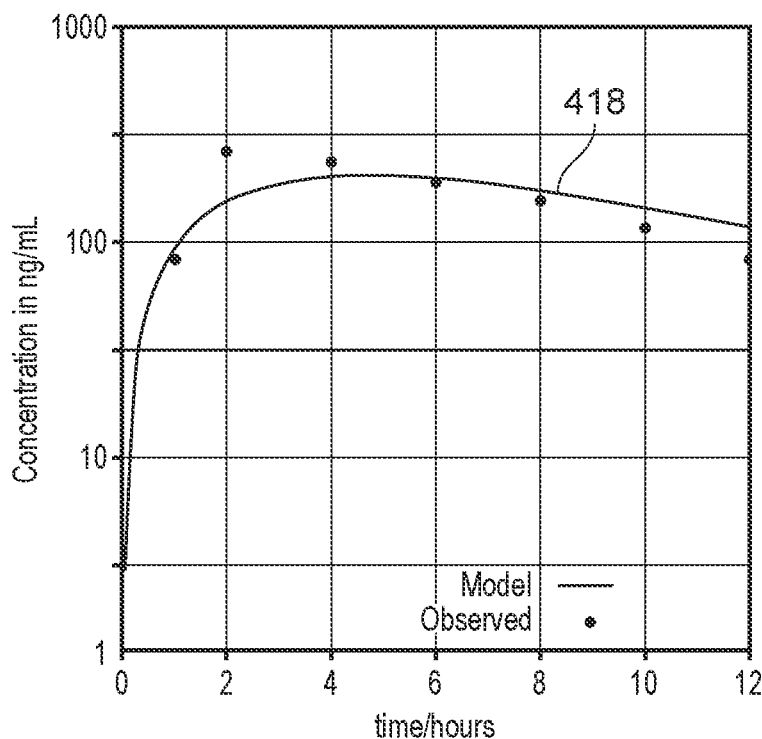
FIG. 4A illustrates a comparison of clinical data for 12-hour population-average Apixaban plasma levels after a single dose of 20 mg in healthy white males and females with a plasma level prediction model according to an embodiment of the present disclosure.

FIG. 4A illustrates the comparison of 12-hour population-average Apixaban plasma levels (point data) after a single dose of 20 mg in healthy white males and females aged 18 to 39 (mean 30.5 years), with the above plasma level prediction model (line data 418) according to embodiments of the present disclosure. The input parameters included Sex=male, Wt=89.0 kg, AGE=30 years, ETHN=white, no co-administered drugs and CrCL=125 mL/min. It can be seen that the model 418 is in good agreement with the experimental data.

Figure 4B:
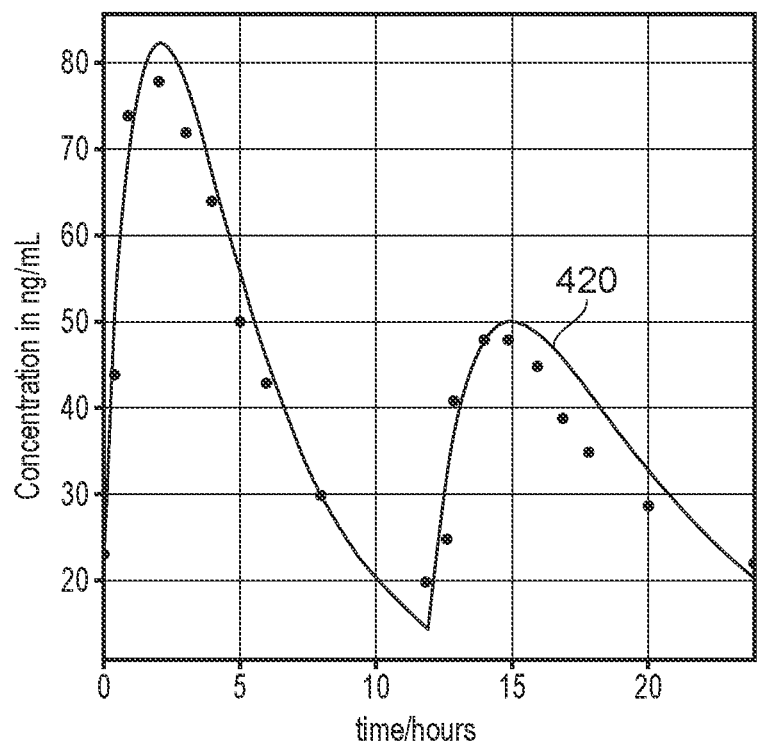
FIG. 4B illustrates a comparison of clinical data for 24-hour population-average Apixaban plasma levels (point data) at steady-state plasma levels for a twice daily dose of 2.5 mg in healthy white males and females with a plasma level prediction model according to an embodiment of the disclosure.

FIG. 4B illustrates the comparison of 24-hour population-average Apixaban plasma levels (point data) at steady-state plasma levels for a twice daily dose of 2.5 mg in healthy white males and females aged 18 to 39 (mean 30 years), with the above plasma level prediction model (line data 420) according to embodiments of the present disclosure. The input parameters included Sex=female, Wt=77.0 kg, AGE=30 years, ETHN=white, no co-administered drugs and CrCL=100 mL/min. It can be seen that the model 420 is in good agreement with the experimental data.

Figure 4C:
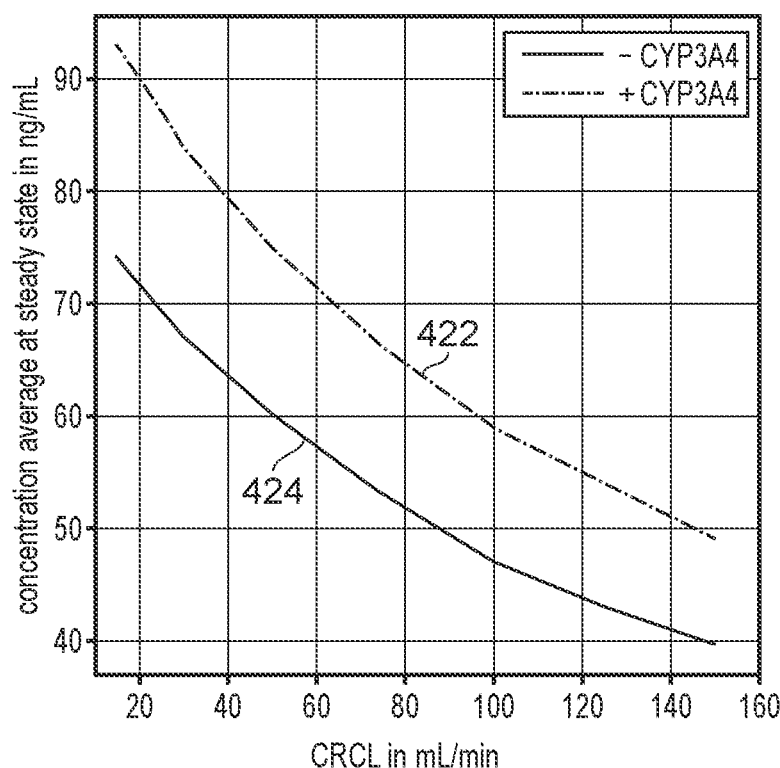
FIG. 4C illustrates the relationship between renal function and steady-state average plasma levels, as determined by a plasma level prediction model according to an embodiment of the disclosure.

FIG. 4C illustrates the relationship between renal function (CrCL) and steady-state average plasma levels, as determined by the above plasma level prediction model for a fixed dose of 2.5 mg twice daily. A first plot 422 shows the variation in plasma level as a function of creatinine clearance in the absence of a CYP3A4 inhibitor. A second plot shows the variation in plasma level as a function of creatinine clearance in the presence of a CYP3A4 inhibitor. Input data for both plots 422, 424 included Sex=male, Wt=85.0 kg, AGE=60 years, ETHN=white. The curves illustrate the significant impact of both renal function and CYP3A4 inhibitors on circulating drug plasma levels.

Figure 4D:
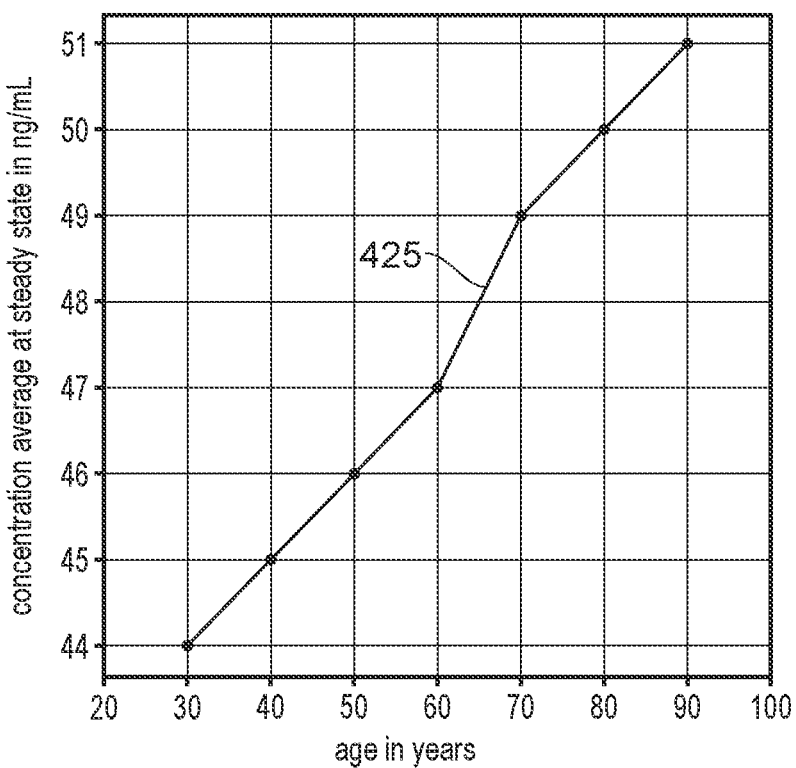
FIG. 4D illustrates the relationship between age and steady-state average plasma levels, as determined by a plasma level prediction model according to an embodiment of the disclosure.

FIG. 4D illustrates the relationship between age and steady-state average plasma levels, as determined by the above plasma level prediction model for a fixed dose of 2.5 mg twice daily. A plot 425 shows the variation in steady-state average plasma level as a function of age. Input data included Sex=female, WT=85.0 kg, CrCL=100 mL/min, ETHN=white. The curves illustrate the impact of age on circulating drug plasma levels.

Figure 4E:
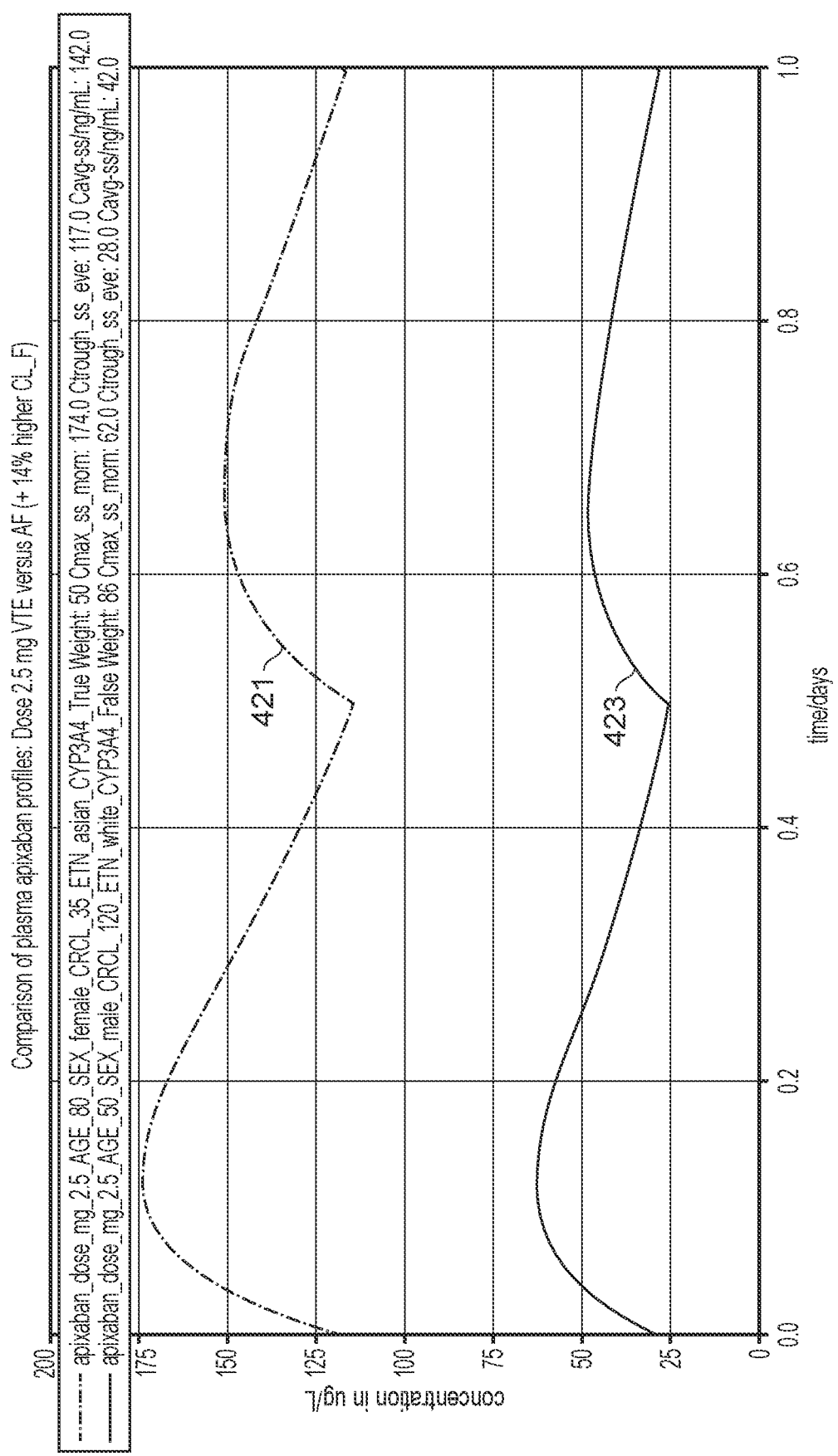
FIG. 4E illustrates simulated steady-state plasma levels for two different patients taking 2.5 mg Apixaban as determined by a plasma level prediction model according to an embodiment of the disclosure.

It can be seen from the above equations for the model and from FIGS. 4A to 4D, that although renal function, age and weight are presently the main parameters used by regulatory agencies to dictate starting doses, there are a number of other co-variates (patient input data) such as CYP3A4 inhibitors (see FIG. 4C) that should be taken into account when computing what trough plasma levels may be attained for a particular patient. This is particularly true when single or multiple extremes are taken into account, as illustrated in FIG. 4E. FIG. 4E illustrates simulated steady-state plasma levels for two different patients taking 2.5 mg Apixaban: (i) a first plot 421 illustrates a subject who is female, South Asian, 80 yrs, 50 kg, CrCL=35 mL/min, is taking a CYP3A4 inhibitor; and (ii) a second plot 423 illustrates a subject who is male, white, 50 yrs, 86 kg, CrCL=120 mL/min and is not taking a CYP3A4 inhibitor. The steady state plasma levels are over 3 fold higher in the elderly subject than the healthy subject (142 ng/mL versus 42 ng/ml). Such "extreme" patients may need a starting dose lower than the 2.5 mg presently available. As discussed below, the provision of a dosage calculator based on a plasma level prediction model can enable: (i) the provision of accurate and precise dosages; (ii) the provision of personalised dosages; (iii) the utilisation of a broad range of patient data, including data never before considered in pharmacometrics modelling; (iv) the provision of dosage monitoring and adjustment; (v) the definition of novel dosage regimens; and (vi) the provision of clot and bleeding risk according to time since last medication taken.

Embodiments of the present disclosure may comprise two-compartment models based on equations 1 to 4 and modified by other expressions for F, Vc and/or Cl derived from other patient studies of Apixaban, including studies conducted using the apparatus and methods disclosed herein. Other embodiments may include simpler single compartment models that do not include the peripheral compartment 303. However, two compartment models can provide more accurate results than single compartment models.

Dosage Calculator

The plasma level prediction model can predict plasma levels throughout the day including peak or maximum plasma levels (Cmax), average levels (Caverage) and/or trough levels (Ctrough) based on the individual patient data. Returning to the method of FIG. 2, the method advantageously implements a dosage calculator derived from the plasma level prediction model enabling calculation of a starting dose (or dose adjustment) using Pharmacokinetic principles.

Returning to FIG. 2, in relation to the second step 214, the method processes the patient data with a dosage calculator derived from the plasma level prediction model. In some examples, the dosage calculator may receive a target plasma level metric and calculate the dosage for administering to the patient by processing the patient data and the target plasma level metric. The target plasma level metric may comprise an ideal therapeutic level (ITL). The ITL may comprise an average plasma level (Caverage) over 24 hours of 40-150 ng/ml, or a more targeted level such as 80-110 ng/ml or 95 ng/ml. The ITL may comprise a trough plasma level (e.g. 34-100 ng/ml). The ITL is intended to provide the best balance between the reduction in risk of thrombosis and embolism balanced against increased risks from haemorrhage. The ITL ranges and values disclosed herein may be illustrative of an optimum balance between thrombosis risk and bleeding risk at a population level. It will be appreciated that other ITL values may be used, such as future values established by parties of experts. Data from the disclosed systems and methods may inform, define or refine an ITL for Apixaban plasma concentration. Such ITL's may be defined for a plurality of patient groups with different risk factors based on personalised target plasma level metrics (See below). The target plasma level metric may relate to other blood plasma metrics such as maximum concentration and may be personalised based on the patient data, as discussed under the "personalised target plasma level metrics" section below.

Dosage Calculator Example 1

In some examples, the dosage calculator may determine a dose of Apixaban for administering to a patient using an analytical analysis based on Pharmacokinetic principles as follows. For example, it has been shown [1] that following a single dose of Apixaban there is a log linear relationship between the maximal plasma level and the dose administered:

$$\log(C\max) = 3.079 + 0.945 \log(\text{Dose}) \quad (\text{Eq13})$$

Similarly the area under the plasma curve (AUC) is a log linear relationship according to equation 5

$$\log(\text{AUC}) = 5.283 + 1.009 \log(\text{Dose}) \quad (\text{Eq14})$$

Average plasma levels (Caverage) can then be calculated by:

$$\text{Caverage} = \frac{AUC}{24} \quad (\text{Eq 15})$$

A similar approach can also be taken to calculate a dose for trough plasma levels. For example, the relationship between the maximum plasma level, Cmax, the trough plasma level, Ctrough and the drug half-life can be written as:

$$Ctrough = Cmax \cdot 0.5^{\frac{t_{decay}}{\text{Half life}}} \quad (\text{Eq 16})$$

where $t_{decay}$ is the time for the drug plasma level to fall from Cmax to Ctrough. The half-life may be calculated from the central compartment volume and the total clearance, which may be determined from the plasma level prediction model. The decay time, $t_{decay}$, may be calculated from the plasma level prediction model. For example, the model may calculate the time from dosage administration to Cmax, $t_{rise}$, and may calculate the decay time, $t_{decay}$=dosage interval−$t_{rise}$. Such an approach may be more favourable in a simpler single compartment model. In some examples, the half-life and/or decay time may be estimated or based on values from previous studies.

An advantage of the analytical approach is that the differential equations (equations 1 to 12) of the plasma level prediction model are not necessarily required and this reduces the processing requirements required for the dosing calculation.

In some examples, analytical dosage calculators may be derived from single compartment plasma level prediction models that may be solved analytically to output a dosage for a particular target plasma level metric.

A modification of this analytical calculator may identify a dose which achieves the closest average or trough plasma level to the ITL without causing Cmax to exceed a particular threshold value and thus minimise the risk of haemorrhage. This modified calculator could be limited to those patients where there is a particular risk of haemorrhage. Cmax may also be controlled with novel dosage forms as discussed further below.

Dosage Calculator Example 2

In some examples, the dosage calculator may implement a two compartment plasma level prediction model utilising all of equations 1 to 4 (and optionally one or more of equations 5 to 12) of the above plasma level prediction model. The dosage calculator may then proceed according to the method of FIG. 5, which illustrates a method of determining a dosage for administering to a patient according to an embodiment of the present disclosure.

A first step 526 comprises setting an initial value of a dosage estimate.

A second step 528 comprises processing the dosage estimate with the dosage calculator to determine a plasma level metric. The plasma level metric may comprise, a maximum plasma level, Cmax, an average plasma level over a dosing interval at steady state, Caverage, (i.e. once the drug has accumulated and stabilised over a number of days), a trough plasma level, a ratio of the maximum to trough plasma levels or any other plasma level metric described herein.

A third step 530 comprises comparing the plasma level metric to the target plasma level metric. The target plasma level metric may comprise the same metric (Cmax, Caverage, trough level) as the plasma level metric.

A fourth decision step 532 comprises determining if a difference in the values of the plasma level metric and the target plasma level metric is within a difference threshold. If not the method proceeds to a fifth step 534 and refines the dosage estimate, before returning to the second step 528.

If the difference in the two values is within the difference threshold, the method proceeds to a sixth step 536 and outputs or indicates the dosage estimate as the dosage for administering to a patient.

In some examples, the loop around the second to fifth steps 528-534 may be performed in an iterative fashion until the values are within the difference threshold. In some examples, the loop may be performed at least two times and a dosage value corresponding to the target plasma level metric may be interpolated. In some examples, the loop may correspond to an optimisation routine.

A disadvantage of dosage calculator example 2 is that the second step 528 requires a lot of processing power for calculating the blood plasma metric using the piecewise time-step differential equations above (equations 1 to 4). As explained in the "Implementations" section below, the method of FIG. 2 may be implemented as one or both of: (i) a software based dosage calculator configured to indicate dosages in a short timeframe (sub-seconds, seconds or minutes) to a health practitioner and/or patient via a personal computing device or the like; and/or (ii) a software based dosage calculator configured to determine a relational mapping between starting dosage, patient data and target plasma level metric. Such a relational mapping may take the form of a look-up table, a nomogram, an analogue computer or the like. Dosage calculator example 2 may be used in the second such implementation. For example, a detailed relational mapping can be determined over a long time frame (hours, days, months) by performing the method of FIG. 5 for a population set of different patient data. The resulting output can provide a detailed mapping between target plasma level metric (e.g. ITL) and starting dose for a range of the key patient data variables (e.g. kidney function, age, ethnicity, sex, genomics, AF indication, medications etc). The relational mapping (e.g. look-up tables) can provide one or more of: (i) a dosage calculator for the first implementation of the method of FIG. 2 (i.e. quick dosage calculation for patient/HCP); (ii) a training data set for a ML dosage calculator (see Dosage Calculator Example 4); (iii) the foundations of a clinical guidelines reference; and (iv) standard dosing regimens for Apixaban products, regulatory labelling, packaging etc.

Dosage Calculator Example 3

A third example dosage calculator may comprise a look-up table derived from the second dosage calculator example. The second step 528 of FIG. 5 can advantageously be performed rapidly using a look-up table approach. In some examples, the look-up tables may be defined to output the dosage for administering to the patient based on received inputs of the target plasma level metric and the patient data, negating the requirement for the process of FIG. 5 and resulting in more rapid dosage calculations.

Dosage Calculator Example 4

In some examples, the dosage calculator may comprise a machine learning (ML) model (also referred to as a ML algorithm) trained using data output from the plasma level prediction model. The data output from the plasma level prediction model may comprise simulated population data. The simulated population data may comprise data output from the plasma level prediction model following processing of a population set of patient data that represents a population variation in the patient data. For example, a Monte Carlo type approach may be used to generate the population set of patient data using known distributions of each parameter type of the patient data (see below).

In some examples, the simulated population data may comprise plasma level metrics output by the plasma level prediction model. In some examples, the simulated population data may comprise dosages for administering to each patient of the population set to achieve a target plasma level. The ML model can be trained using the simulated population data to provide a ML plasma level prediction model and/or a ML dosage calculator.

Figures 6, 7:
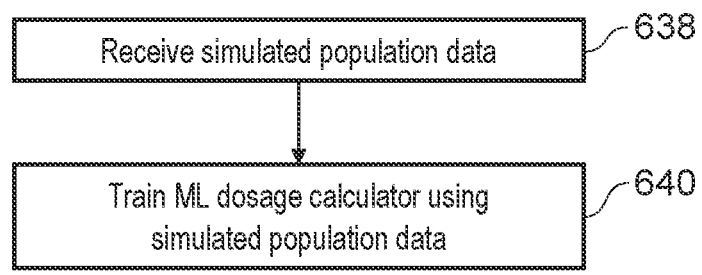
FIG. 6 illustrates a method of generating a ML dosage calculator according to an embodiment of the present disclosure.
FIG. 7 illustrates a sub-sample of simulated population data.

FIG. 6 illustrates a method of generating a ML dosage calculator (or ML plasma level prediction model) according to an embodiment of the present disclosure.

A first step 638 comprises receiving simulated population data calculated using a plasma level prediction model.

A second step 640 comprises training the ML dosage calculator using the simulated population data.

The method may comprise calculating the simulated population data using the plasma level prediction model. For example, the method may comprise: (i) defining simulated patient data for a simulated patient population comprising a plurality of simulated patients; and (ii) calculating plasma level metrics for each of the plurality of simulated patients using the plasma level prediction model to define the simulated population data. The simulated population data may comprise the simulated patient data and the calculated plasma level metrics.

The simulated patient population may comprise at least 100,000 simulated patients, at least 1,000,000 simulated patients or at least 10,000,000 simulated patients. Defining the simulated patient data may comprise: (i) receiving population distributions for each parameter type of patient data (e.g. CrCL, age, weight, other medications, etc); and (ii) generating the plurality of simulated patients by probabilistic based selection of each parameter type according to the respective population distribution. For example, a Monte Carlo type analysis may be used to define the simulated patient data. In other examples, the simulated patient data may comprise a more methodical sweep of the parameter space defined by the patient data. In some examples, the simulated patient data may also include a simulated dosage amount given twice daily. The simulated patient data (including the simulated dosage) can be processed using the plasma level prediction model to obtain the simulated population data comprising a simulated plasma level metric. FIG. 7 illustrates a sub-sample of simulated patient data comprising: a simulated dose 742 and simulated patient data 744 (age, sex, weight, ethnicity, CRCL,), CYP3A4 inhib).

Following generation of the simulated population data, the ML dosage calculator can be trained using the simulated population data. The ML dosage calculator may comprise any known ML architecture such as an artificial neural network or a generative model. In some examples, real patient data, e.g. from a clinical study or an ongoing dosage and monitoring program, may be added to the simulated population data to form the ML training data. The real patient data may comprise patient dosage, patient input data and measured drug plasma levels. The ML training data may comprise weightings for each patient data set, with a higher weighting assigned to real patient data than to simulated patient data.

Figure 5:
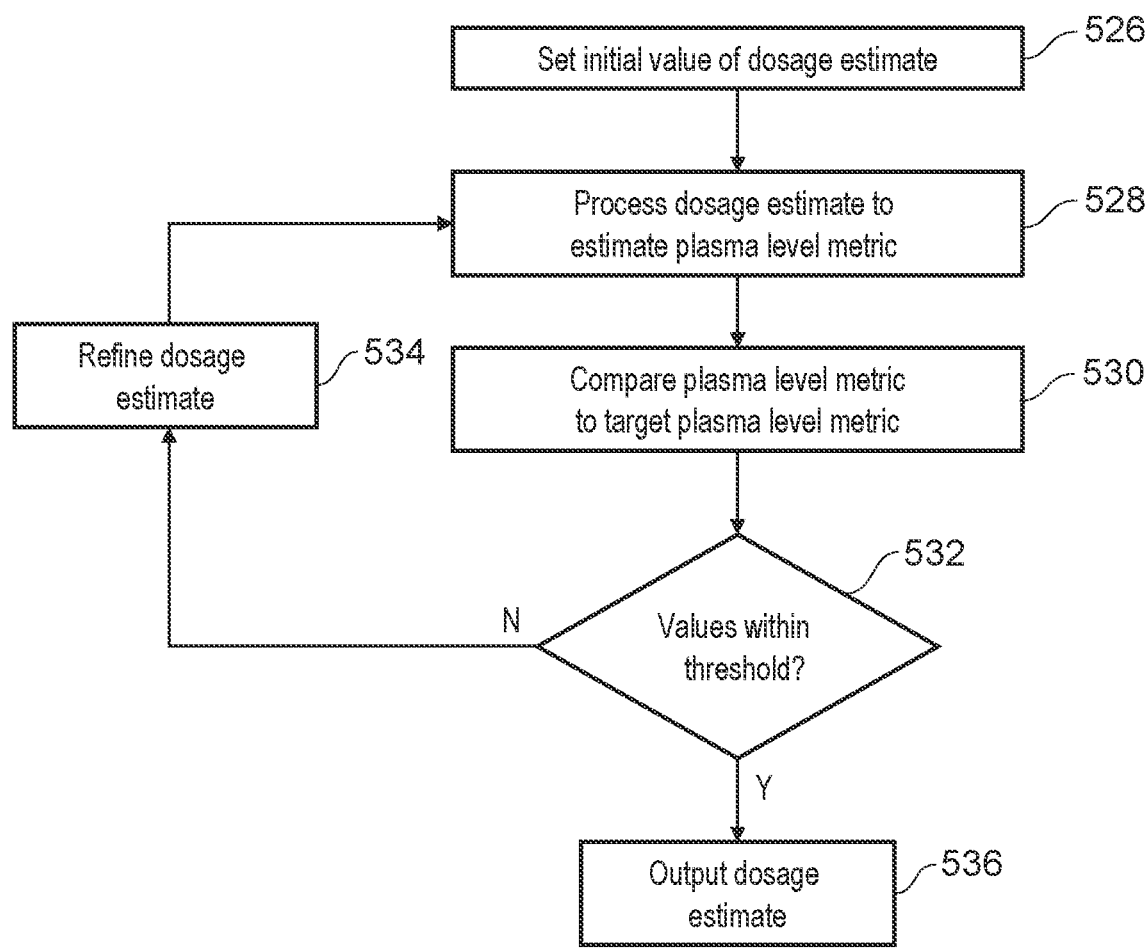
FIG. 5 illustrates a model of determining a dosage for administering to a patient according to an embodiment of the present disclosure.
Figure 8:
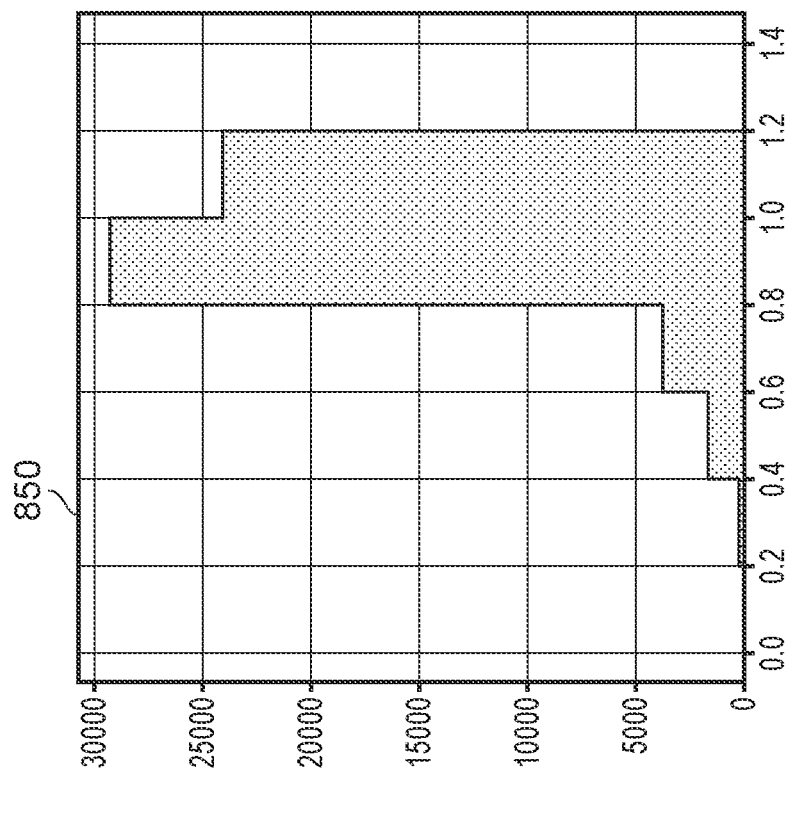
FIG. 8 illustrates validation results of a dense neural network based ML dosage calculator according to an embodiment of the present disclosure.
Figure 8:
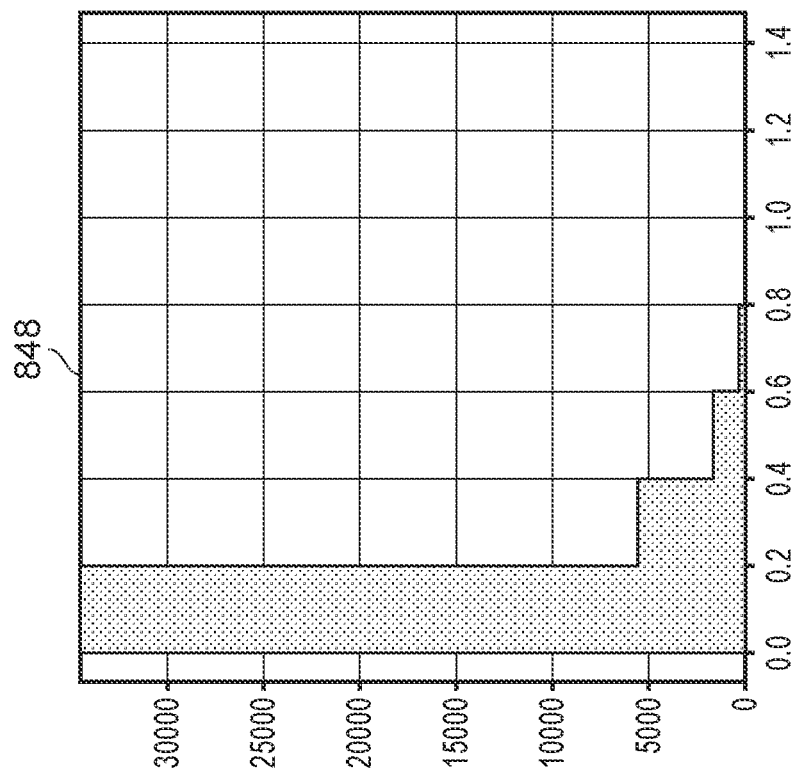

In some examples, the ML dosage calculator may replicate the plasma level prediction model and determine plasma level metrics for a particular dose and then revise the dosage estimate until the plasma level metric satisfies a target plasma level metric (e.g. ITL) to obtain a dosage for administering to a patient (in the same way as FIG. 5). FIG. 8 illustrates the validation results of a dense neural network based ML dosage calculator. The ML dosage calculator was trained on simulated population data for 1,000,452 simulated patients. The ML dosage calculator was then tested on simulated population data for ~100,000 simulated patients. The simulated population data was generated using plausible individual demographic, physiological or interacting drug combinations for the simulated patient data, for example: renal clearances from 30-200 ml/min, body weight from 50-120 kg, age 40-90 yr, with and without co-administered drugs etc. The test simulation data included CrCL levels not generated in the training data set to provide extra rigour. The simulated population data was obtained using the plasma level prediction model described above in relation to equations 1 to 11. An ITL range or "optimum window" was defined as AUC plasma levels ranging from 1000 to 3600 ngh/mL. This ITL range can provide a best balance between the reduction in risk of thrombosis and embolism balanced against increased risks from haemorrhage from the Apixaban administration. The optimum window can be similarly defined as a trough plasma from 34 ng/ml to 100 ng/ml (e.g. by mapping AUC to trough level using the predicted plasma time profiles of the plasma level prediction model). The optimum window can also be mapped to an average plasma level from 40 ng/ml to 150 ng/ml (using equation 14).

The validation results are divided into two plots: (i) a first plot 848 illustrating the ML dosage calculator's prediction of whether a dosage is optimal for dosages identified as non-optimal by the plasma level prediction model; and (ii) a second plot 850 illustrating the ML dosage calculator's prediction of whether a dosage is optimal for dosages identified as optimal by the plasma level prediction model. The x-axis scale for both plots 848, 850 is a prediction confidence of the ML model as to whether the plasma level is within the optimum window, with 0 corresponding to steady-state plasma levels falling outside the optimum window, and 1.0 corresponding to steady-state plasma levels falling inside the optimum window. A threshold of 0.4 is set to divide the classification into optimal and non-optimal doses. The ML dosage calculator correctly identifies dosages as optimal or not for over 99.3% of the simulated population data. While not infallible, it will be appreciated that further refinements and improvements can be made, such as improvement of training data (more data, more realistic data, real data), and that the performance may be superior to the subjective assessment of dosage by a HCP (e.g. a clinician) who may not have a complete picture of the patient data.

As noted above, a ML dosage calculator that outputs a plasma level metric by processing a particular dose and patient data can be used in the method of FIG. 5 to determine a dosage for administering to a patient.

Figure 9:
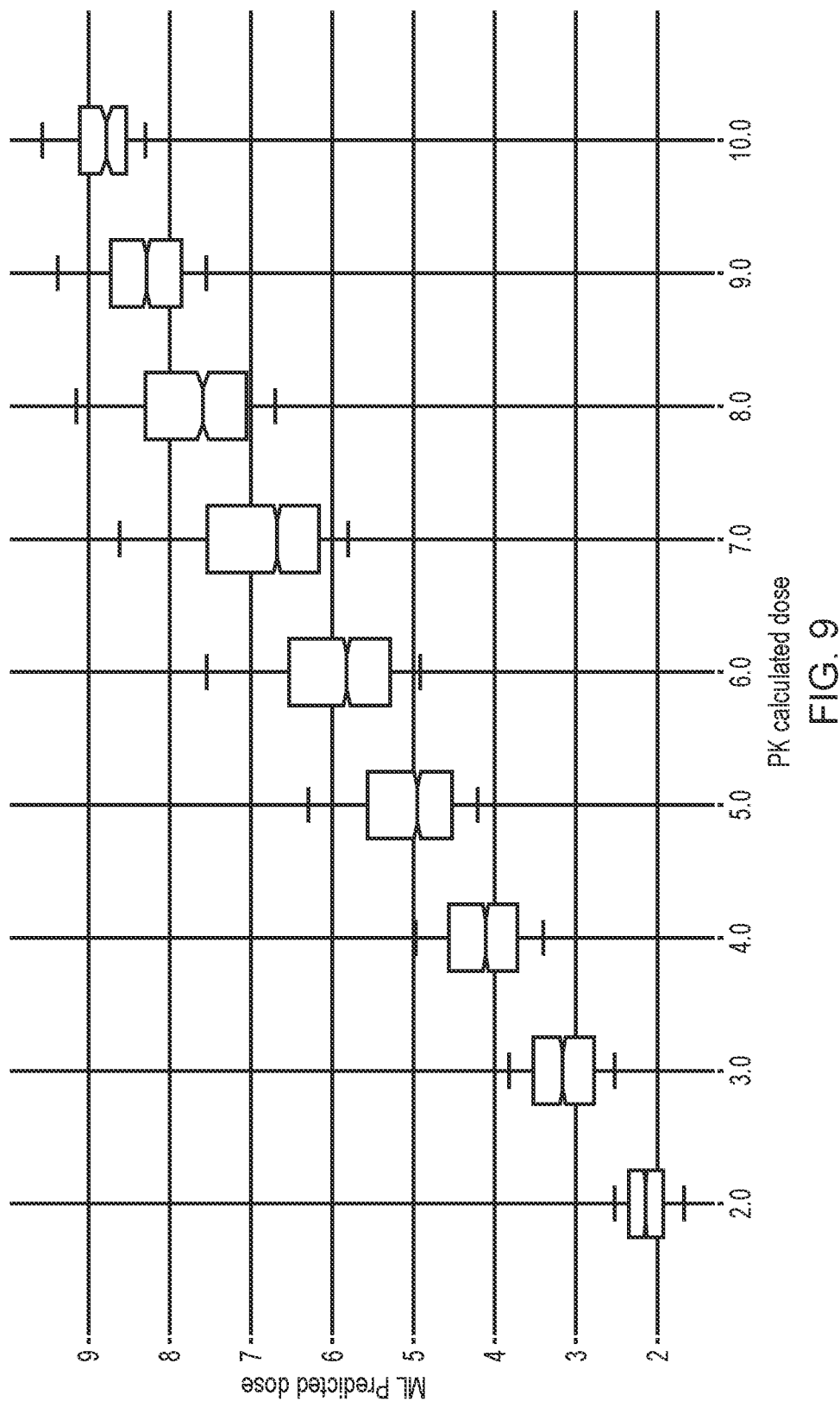
FIG. 9 illustrates validation results of a dense neural network based ML dosage calculator according to another embodiment of the present disclosure.

In some examples, the ML dosage calculator may receive a target plasma level metric and patient data, and directly determine a dosage for administering to the patient. FIG. 9 illustrates the validation results of a dense neural network based ML dosage calculator. The ML dosage calculator was trained on simulated population data for 42,822 simulated patients. The ML dosage calculator was then tested on simulated population data for simulated patients. The simulated population data was obtained using the plasma level prediction model described above in relation to equations 1 to 11. The test population data was restricted to data for which the plasma level prediction model indicated a trough plasma level in the optimum window. The x-axis corresponds to the dosage used in the plasma level prediction model to provide the trough plasma level in the optimum window. The y-axis corresponds to the dosage predicted by the ML dosage calculator to provide the trough plasma level in the optimum window. The ML dosage calculator only outputs a limited spread in recommended dosage indicating strong performance of the direct ML dosage calculator. As a further validation, the dosages output from the ML dosage calculator were input to the plasma level prediction model to provide a calculated plasma level. The resulting trough plasma levels are indicated in table 3. The results show that the ML predicted doses yield>99% of Ctrough estimates falling within the optimum window (Ctrough (34-100 ng/ml)) with only a small percentage of doses (0.9%) falling just above (but less than 120 ng/mL).

TABLE 3

Trough plasma level distribution for ML calculated dosages

| Ctrough ng/mL | ML predicted % in range |
| --- | --- |
| 50 | 0.4 |
| 60 | 21.8 |
| 70 | 28.1 |
| 80 | 22.3 |
| 90 | 14.3 |
| 100 | 12.3 |
| 110 | 0.9 |
| 120 | 0.0 |

A major advantage of the ML dosage calculator is that it can operate at significant speed relative to the two-compartment differential equation model (equations 1 to 11) underpinning the training data. The efficient processing means the ML dosage calculator requires much less processing power than the model of equations 1 to 11 enabling deployment of the ML dosage calculator at scale to HCPs and/or patients, e.g. via a cloud platform and/or personal computing devices. Other advantages of the ML dosage calculator include: (i) a wealth of data available at speed including optimised dosages and plasma level metrics, such as Ctrough, Caverage, Cmax, Cmax/Ctrough ratios or time profiles (similar to the profiles of FIG. 4B). Such time profiles can be used to indicate a time dependent haemorrhage or clotting risk to a patient (see "Outputs" section below); and (ii) precise, personalised and accurate dosages. Furthermore, the model allows for continuous learning, including incorporation of new adjustment parameters as data accrues. Such adjustment may be performed in regulated phases or stages to ensure ongoing regulatory compliance and safety.

In some examples, a ML dosage calculator may be locked following training and validation, in that the ML dosage calculator will not "learn" from any future data. Such an approach can improve safety and enable easier regulatory approval by ensuring that the ML dosage calculator does not evolve into an unsafe regime based on an error in further training data. Alternatively, in some examples, such as applications where safety requirements may be more relaxed, for example where the drug is used in terminal illnesses, a highly monitored environment, or a clinical situation in which the HCP has no alternative, the ML dosage calculator may be free to evolve and use live data as further training data to provide a more accurate dosage calculator.

The above description relating to the generation, use and advantages of a ML dosage calculator is not limited to Apixaban. Embodiments of the present disclosure can include the above described generation, use and advantages for any drug whose absorption and clearance can be modelled by pharmaco-kinetic modelling and/or pharmaco-dynamic modelling such as two-compartment, differential equation based models. For example, other drugs may be modelled using similar PKPD models to those of equations 1-4. Specific refinements, similar to equations 5 to 11 can be provided by corresponding real patient studies and PKPD analysis for the corresponding drug and contributing individual patient data (which may differ from the patient data listed for Apixaban). In some examples, the central compartment may represent locations other than blood plasma, such as tissues with high blood flow e.g. liver, heart, lungs etc. As a result, the dosage calculator may be generated from a PKPD model for the drug that predicts a time dependence of an appropriate PKPD metric. For Apixaban the PKPD metric is a plasma level metric, however the PKPD metric could include other metrics such as drug concentration in the central compartment (e.g. liver, muscle tissue etc). A ML dosage calculator trained using simulated population data from a two-compartment model advantageously produces an efficient dosage calculator that does not suffer from the huge processing requirements of the underlying differential equation based model and can therefore be deployed at scale to patients and/or HCPs. In particular, embodiments of the present disclosure include the method of FIG. 6 for any drug that can be simulated using PK and/or PD modelling, including a two-compartment model.

A further advantage of training a ML dosage calculator with simulated population data from a verified PKPD model relates to the safety, confidence and regulatory approval of ML models. As illustrated by the above examples, a large number of patients may be required to successfully train and maximise the advantages of a ML dosage calculator. Obtaining patient data for the equivalent number of real patients for a particular drug would be infeasible or at best prohibitively time consuming and expensive. As a result, ML models can struggle to obtain regulatory approval, particularly if part of the training phase is proposed to be conducted as part of deployment because such an approach lacks predictability. Embodiments of the present disclosure relate to training and verifying a ML model with a large simulated patient data set that is based on a verified and accepted analytical model developed from real (and attainable) patient data. The resulting ML dosage calculator is safe, predictable and can be locked to avoid any further learning (with a possible exception for defined and regulatory approved update points).

A yet further advantage of training a ML dosage calculator is that it can provide outputs for combinations of co-variants that are not well represented in original patient data set. In this way, the ML dosage calculator can artificially enrich specific cases of interest and improve the weighting and consideration of less common combinations of characteristics thereby reducing bias and inferior predictions.

Furthermore, deploying the safe, predictable, efficient ML dosage algorithm at scale for patients and HCPs can enable the collection of real patient data (including measured PKPD metrics such as drug plasma levels (see "Ongoing Treatment Management" section below)). Such deployment would be infeasible with a two-compartment differential equation based PKPD model due to the processing constraints. The collected real patient data can then be used to evolve the ML dosage calculator and/or the PKPD model to further improve the accuracy and precision of the dosage calculator.

In some examples, training the ML dosage calculator may be performed in two steps. In a first pre-training step, the ML dosage calculator may be trained using simulated population data, as described above. A second refinement step may comprise training the ML dosage calculator further using refined training data. In some examples, the refined training data may comprise clinical data from real patients comprising patient data, associated drug dosages and resulting drug plasma metrics. In some examples, the refined training data may relate to a different drug that has a similar PKPD pathway to the drug used in the first pre-training step. In this way, ML dosage calculators can be pre-trained in a generic way and then refined using real world patient data and/or for a related drug with a similar underlying structure.

Patient Data

Current regulatory guidelines for Apixaban dosing only account for a limited amount of patient parameters. In the EU, the starting dose is based on weight, age, kidney function and mode of treatment (preventative or reactive). Dosing guidelines can be particularly complex for paediatrics. In the USA, dosing guidelines are based on the renal function of the individual but doesn't take into account patient demographics nor the large inter-subject variability in drug absorption described above. However because only two doses are available, dosing flexibility is limited.

The above described plasma level prediction models indicate that a kidney function metric, specifically creatinine clearance, CrCL, is a significant contributing factor to drug plasma level variability among the patient population. Age, weight, sex, ethnicity, AF indication, and other medications (specifically, proton pump inhibitors and CYP3A4 inhibitors) can also all modulate the circulating drug level in the blood plasma.

Returning to the first step 212 of FIG. 2, in the simplest embodiments, the patient data comprises the kidney function metric. In such embodiments, average population values, or surrogate substituted values, may be used for the other parameters involved in the above dosage calculators and plasma level prediction models. In some embodiments, the patient data may include one or more of the other patient parameters defined in equations 1 to 12, namely: age, weight, sex, ethnicity, genomics (e.g. (e.g. CYP3A4/5 and the ABCG2 gene), and other medications. In some examples, the patient data may include the most easily accessible data, such as age, weight, sex, ethnicity, AF indication, genomics and co-medications. In some examples, parameters requiring a specific medical test such as CrCL may be estimated using surrogate substitution as described below.

Patient weight can present a particular issue with present guidelines as international guidelines for Apixaban only mention below 60 kilograms. However, a patient who is just over the weight limit, e.g. 61 kg, but with who is elderly, female, Asian and taking CYP3A4 inhibitors may require a reduced dosage. By including weight as a patient data parameter, the dosage calculator can determine a personalised dosage in a holistic way and avoid the effects of the binary 60 kg threshold. In addition, the patient population is increasingly overweight and there is no knowledge as to what to do for overweight subjects in terms of DOACs. By including weight as a parameter of the patient data, the dosage calculator can advantageously account for patients with excessive weight.

Additionally, endothelial changes, with disease or just age, can affect absorption of Apixaban. By including age as a parameter of the patient data, the dosage calculator can advantageously account for the age dependency on plasma drug levels.

The above described plasma level prediction models and calculators can require values for age, sex, CrCL, weight, ethnicity, genomics, AF indication and co-medication drugs. While the use of specific interfering drugs is likely to be known, along with weight, age, sex and, in some circumstances, CrCL level may not be known without prior testing.

In some examples, the values of CrCL may be provided by population based surrogate estimates. For example, an estimated creatinine clearance rate (eCCR) can be provided by the Cockcroft-Gault formula. Creatinine clearance can be estimated using serum creatinine levels. The Cockcroft-Gault (C-G) formula uses a patient's weight (kg) and gender to predict CrCL (mg/dL). The resulting CrCL is multiplied by 0.85 if the patient is female to correct for lower CrCL in females. The C-G formula is dependent on age as its main predictor for CrCL. The C-G formula can be written as:

$$eCCr = \frac{((140 - \text{Age}) \times \text{Mass} \times [0.85 \text{ if female}])}{\left[\text{Serum Creatinine}\left(\frac{mg}{dl}\right)\right]}$$

Serum creatinine can be measured, derived from age related change and potentially further revised according to other diseases or conditions. In the absence of a direct measurement of CrCL, the eCCR can be substituted for CrCL in the dosage calculations described herein.

Other Patient Data Parameters

The present disclosure may encompass other plasma level prediction models and dosage calculators that are available now or may be available in the future following appropriate patient studies. Therefore, the patient data may include one or more patient parameters (further to those listed above) that may affect the absorption or clearance of the drug into and from the body.

For example, the patient data may also include medications other than those specifically mentioned above, including: a calcium channel blocker; antifungal such as ketoconazole, diltiazem and rifampicin. The patient data may also comprise Cytochrome P450 data (other than the CYP3A4 discussed above). Cytochrome P450 are a suite of enzymes which mainly occur in the liver, but can also be found throughout the body, which metabolise drugs. In some examples, an administered drug (such as the CYP3A4 inhibitors discussed at length above) can reduce or increase the activity of these enzymes which may result in other co-administered drugs having higher or lower plasma levels. In this way, other drugs can have effect on Apixaban blood levels by modifying how it is metabolised. Therefore, models and calculators utilising other Cytochrome P450 data can account for drug interactions.

Patient compliance can also affect drug concentration levels. Patient dosage compliance may indicate a patient's propensity to take their medication in accordance with a prescribed regimen. The plasma level prediction model and dosage calculator may be refined to account for patient compliance (e.g. via future patient trial). The method may include monitoring a patient compliance and adjusting the dosage accordingly.

One or more of these further patient data parameters that can affect the drug concentration in the body may be incorporated into the plasma level prediction model and/or dosage calculator via an appropriate patient trial. Patient data, including the one or more (new) patient parameters, together with patient dosage (amount and time) and directly measured plasma level metrics can be recorded to evolve the plasma level prediction model and/or dosage calculator to account for the additional dependency of the one or more new patient parameters accordingly.

The patient data may comprise yet further patient data parameters. For example patient data parameters may include those that can influence personalised target plasma level metrics as discussed in the relevant section below. Further patient data parameters may include side effect reporting (see section "side effect monitoring" below), a time a dose was taken and other examples described herein.

The patient data may include patient data parameters that may influence a risk of haemorrhage and/or a risk of thrombosis. Such patient data may be used to indicate the risk to the patient and/or to set personalised target plasma level metrics, as discussed further below. Therefore, according to embodiments of the present disclosure, the patient data may include other patient parameters that may be endothelial function drivers. These include one or more of: smoking history; alcohol intake; a patient thrombosis history; a patient haemorrhage history; a patient cancer history; a patient cardiovascular history; a patient metabolic history; a patient platelet count; patient genetic determinants; a patient haematocrit; a patient liver function; a patient blood pressure; patient co-conditions; patient activity level; patient dosage compliance; family history of thrombosis; family history of strokes; family history of bleeding (e.g. anaemia); and family history of hypertension.

The patient haemorrhage history may include haemorrhage events indicating a severity and time of event. The patient haemorrhage history may relate to the endothelial state or bleeding propensity such as propensity to superficial bruises on arms and legs and other measurements of skin elasticity. Other methods for assessing blood vessel data and/or endothelial state include image analysis of retinal vessels from fundal photography. The flexibility of the model facilitates incorporation of surrogate measures of endothelial state that may be incorporated into future plasma level prediction models, for example by assessment and training using Machine Learning capabilities.

The patient thrombosis history may include thrombosis events indicating a severity and time of event. The family history of thrombosis may include first degree relatives and may include those with an age less than 50 years.

The patient history of at risk events may include recordings of intermittent atrial fibrillation events, including their duration, time of occurrence and rate. Such recordings may be provided from cardiac data from a smart watch.

In relation to cancer history, cancer has a particularly high thrombotic risk because the endothelium becomes very activated, which then releases various coagulation factors. Even with treatment with DOACs, thrombosis can commonly occur in cancer settings, with a high recurrence rate of approximately 17 to 18%, yet also a risk of major haemorrhage of 20%. This is particularly so with certain cancers such as lung, pancreas and colon, demanding even more patient monitoring and precise dosing. Overall, it is estimated that even in the best centres, only one third of patients with thrombosis get well managed and that elsewhere where management is by a general physician or respiratory physician, optimal management is received in less than 10% of cases. As described below, embodiments of the disclosure can include a personalised target plasma level metric for cancer patients to account for their unique PK-PD. As also described below, embodiments of the disclosure may include enhanced monitoring to calibrate and/or personalise the plasma level prediction model and dosage calculator.

Patient genetic determinants may supplant, refine or improve the model or calculator classification of ethnicity (for example).

The patient activity level may represent personal risk exposure, for example an indication that the patient partakes in hazardous activities or other lifestyle factors, such as recreational drugs, physical activity, etc.

The patient co-conditions may include an indication of whether the patient suffers from AF and an extent of the AF. If the extent of the AF is particularly bad with dizzy spells fainting and tachycardia then higher doses would be warranted.

If the patient has a family history of stokes or hypertension then higher dosing with some bleeding may be more tolerated.

The patient metabolic history may be indicative of diabetes which can modify coagulation and blood circulation as a comorbidity.

Receiving Patient Data

Patient data may be received by one or more of: manual data entry, by either a patient, HCP or third party at a computing device such as a personal computing device; data from medical records stored on a database or similar; and receiving physiological measurements, for example from medical devices or clinical databases. For example, patient data may include cardiac data from a smart watch that can indicate periods of AF.

Implementations

The method of FIG. 2 may be implemented as one or both of: (i) a software based dosage calculator configured to determine a relational mapping between starting dosage, patient data and target plasma level metric; and (ii) a multi-use deployed software based dosage calculator configured to indicate dosages in a short timeframe (sub-seconds, seconds or minutes) to a health practitioner and/or a patient via a personal computing device or the like.

Relational Mapping Implementation

A relational mapping between patient data, dosage and one or more plasma level metrics may take the form of a look-up table, a nomogram, an analogue computer or the like. Any of the above described dosage calculator examples (or a combination of them) may be used to determine the relational mapping. For example, a detailed relational mapping can be determined by performing the methods of FIG. 5 or FIG. 6 for a population set of different patient data. The population set of patient data may include simulated patient data and/or real patient data. The resulting output may include a detailed mapping between one or more target plasma level metrics (e.g. ITL) and starting dose for a range of the patient data variables (e.g. kidney function, age, ethnicity, sex, medications etc). The relational mapping (e.g. look-up tables) can provide one or more of: (i) a dosage calculator for the implementation of the method of FIG. 2 (i.e. quick dosage calculation for patient/HCP); (ii) a training data set for a ML dosage calculator; (iii) the foundations of a clinical guidelines reference; and (iv) standard dosing regimens for Apixaban products, labelling, packaging etc.

The relational mapping implementation may be implemented using any known computing device architecture such as a stand-alone computing system or a networked computing system such as that of FIG. 10 described below in relation to the second implementation.

Multi-Use Deployed Software Implementation

Figure 10:
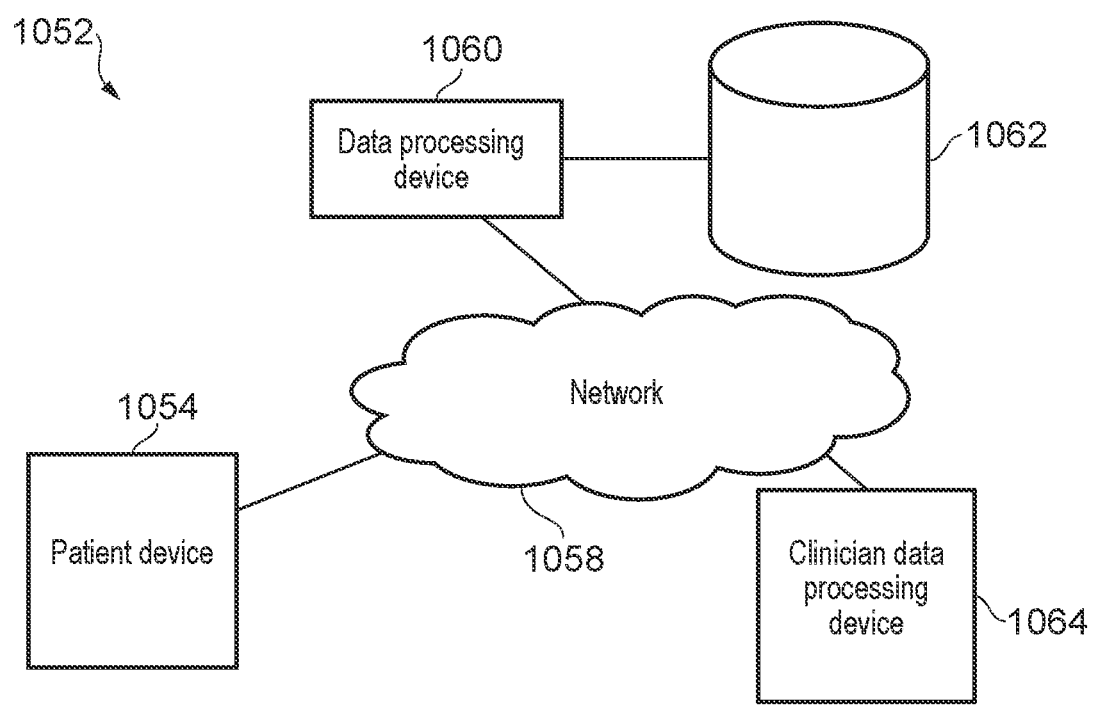
FIG. 10 illustrates a system suitable for carrying out any of the computer implemented methods described herein.

FIG. 10 illustrates a system suitable for carrying out the multi-use deployed software implementation (also referred to herein as the digital app) and any of the computer implemented methods described herein, including the method of FIG. 2. System 1052 includes a patient device 1054. The patient device 1054 may comprise one or more processors configured to: receive the patient data; process the patient data with a dosage calculator to determine the dosage of Apixaban for administering to the patient, wherein the dosage calculator is derived from a plasma level prediction model; and indicate the dosage.

In the illustrated embodiment, patient device 1054 is a smartphone. However, the invention is not limited in this respect and the patient device 1054 can take many other forms, including but not limited to a mobile telephone, a tablet computer, a desktop computer, a voice-activated computing system, a laptop, a gaming system, a vehicular computing system, a wearable device, a smart watch, a smart television, an internet of things device and a medicament-dispensing device.

The patient device 1054 may be configured to gather one or more parameters of the patient data. The patient data can be obtained via manual data entry using a human interface device of patient device 1054 and/or from a remote source via the network 1058.

The patient device 1054 may comprise a memory (not illustrated) for storing the patient data and/or outputs of the dosage calculator. Such data may also be stored on a database 1062 as networked or cloud-based data storage.

The patient device 1054 may have one or more applications (or apps) installed on a storage medium associated with the patient device (not shown). The one or more apps may be configured to perform any of the computer implemented methods disclosed herein. The one or more applications may be configured to assist the patient in providing the patient data and/or may include the dosage calculator for processing the patient data. The one or more applications may be downloaded from a network, for example from a website or an online application store.

In this example, the system 1054 further comprises a data processing device 1060 that is communicatively coupled to the patient device 1054 via the network 1058. In the illustrated embodiment network 1058 is the internet, but the invention is not limited in this respect and network 1058 could be any network that enables communication between patient device 1054 and data processing device 1060, such as a cellular network or a combination of the internet and a cellular network.

The data processing device 1060 may supplement the patient device 1054 and perform one or more steps of any of the computer implemented methods disclosed herein. For example, in some embodiments, the patient device 1054 may receive the patient data and provide the patient data to the data processing device 1060. The data processing device 1060 may then process the patient data with the dosage calculator to determine the dosage for administering to the patient. The data processing device 1060 may then provide the dosage to the patient device 1054 or a HCP device 1064 (also referred to as clinician device 1064) either or both of which may indicate the dosage. In this way, the data processing device 1060 provides networked, server based or cloud based, processing capability to the system for performing the computer implemented methods.

The data processing device 1060 may be coupled to the database 1062 that can store the patient data and/or the outputs of the dosage calculator.

In this example, the system 1052 includes a clinician data processing device 1064 that is communicatively coupled via network 1058 to the patient device 1054 and the data processing device 1060. The clinician data processing device 1064 may be broadly similar to patient device 1054, offering a similar set of functionality. Specifically, the clinician data processing device 1064 enables patient data to be collated or received. Clinician data processing device 1064 is contemplated as being physically located at a HCP's premises during its use, such as a clinic, a doctor's surgery, a pharmacy or any other healthcare institution, e.g. a hospital. Clinician data processing device 1064 may include one or more sensors, and/or be configured to control one or more separate sensors, which sensors are capable of gathering information about the patient, e.g. a blood pressure sensor.

It is also contemplated that clinician data processing device 1064 is typically used by a medically trained person with appropriate data security clearance, such that more advanced functionality may be available than via the patient device 1054. For example, the clinician data processing device 1064 may be able to access a medical history of the patient, generate a Apixaban prescription for the patient, place an order for medication, etc. Access to functionality may be controlled by a security policy implemented by a local processor or data processing device 1060.

The data processing device 1060 and/or the clinician device 1064 may have an application installed that is compatible with or the same as the application installed on the patient device 1054.

It will be appreciated that the various steps of the computer implemented methods disclosed herein may be performed in any combination by any of the one or more processors in the patient device 1054, the data processing device 1060 and the clinician device 1064. For example, all steps may be performed by the clinician device 1064 which receives one or more parameters of the patient data locally, from the patient device 1054 or another remote device via the network 1058 and optionally via the data processing device 1060. In a further example, all steps may be performed in a networked back-end on data processing device 1060, with patient device 1054 and clinician device 1064 acting as human interfaces for gathering and indicating data. In a yet further example, all steps may be performed on patient device 1054 with clinician device 1064 merely gathering relevant data from the patient device 1054 for informing or directing the HCP.

It will also be appreciated that one or more of the components of the system 1052 could be omitted depending upon the application. For example, at a clinic setting, the disclosed computer implemented methods could be performed solely on the clinician device 1064. Alternatively, the methods could be performed solely on the patient device 1054 in a domestic setting.

The dosage calculator may be deployed to any of patient device 1054, data processing device 1060, and clinician device 1064 as a digital app. The digital app may indicate to the HCP a dose (starting dose, continuing dose or revised dose, timing of dose) for administering to a particular patient based on computed changes in drug levels to achieve the Ideal Therapeutic Level (ITL).

The digital app may also summarise important factors (other patient data) that affect thrombosis and bleeding and present this to the HCP. These factors can include thrombosis and haemorrhage history, cancer history, pattern of any falls, pattern of renal function and liver function, pattern of platelet count, haematocrit, platelet and blood transfusions and age of patient. The app may also recommend a follow up pattern and prompt for any missing information.

Outputs

Dosage Outputs

In relation to the second and third steps of FIG. 2 relating to determining and indicating the dosage for administering to the patient, the dosage determination and indication may be performed in a number of ways.

The indicated dosage may comprise a starting dosage for a patient beginning Apixaban treatment, a continuing dosage confirming that a patient taking Apixaban is dosed at a correct level, or a revised dosage suggesting that a patient's dosage should be adjusted in view of updated patient data (discussed further below under "Ongoing Treatment Management" section).

Wherever dosage is used, this refers to both amount administered, form of medicament (e.g. immediate or controlled release), time taken in relation to food and other events, and periodicity.

In some examples, determining the dosage may comprise: (i) processing the patient data with the dosage calculator to determine an ideal dosage regimen; and (ii) selecting the dosage for administering to the patient from a selection of available dosage regimes, based on the ideal dosage regimen. For example, the second step of the method of FIG. 2 may comprise selecting a dosage amount from the available dosage amounts of 2.5 or 5.0 mg. For some patients, the method may determine and indicate a higher dosage at night and a lower dosage in the morning, so that Cmax occurs at a lower risk time (e.g. in a patient with frequent falls), with the method computing the optimal overall dosage to achieve sufficient clot prevention at all times.

As described below, the present disclosure encompasses novel dosage forms that increase the flexibility in selecting the dosage amount and selecting the dosage amount may comprise selecting dosage amounts that are: increments of 0.1 mg, 0.5 mg, 1.0 mg, 2.5 mg or 5.0 mg. Selecting the dosage regimen may also comprise selecting dosage forms such as liquid formulations or micro-granule formulations as described below.

Determining and indicating the dosage regimen may comprise determining and indicating one or more of: a dosage amount; a dosage time; a dosage frequency; and/or a dosage type. The dosage frequency may comprise twice daily as is the current standard for DOACs. However, the disclosure also encompasses other dosage frequencies including once daily or less than daily which can improve patient compliance and multiple times daily which can reduce the maximum plasma level, Cmax. The method can determine and indicate that for certain patients the medication should only be taken every other day (for example if creatinine clearance is very low), or three times per day (for example if creatinine clearance very high). Or for other patients the method can determine and indicate that twice daily dosing will result in unacceptably risky Cmax plasma levels to achieve a desired Caverage or Ctrough, and therefore either a slow release formulation should be given or an increased frequency of dosing with a lower dosage form.

The dosage time may comprise a time for the patient to take their medication. The dosage time may be provided as simple reminder prompts to a patient to take their medication. The dosage time may also be specific to an event such as upcoming or recently performed surgery. The dosage type may relate to different dosage forms such as solid dose, liquid dose or micro-granule formulation.

Novel Dosage Forms

The disclosed plasma level prediction models, dosage calculators, digital apps and associated methods can encompass dosage amounts, formulations and regimens beyond those currently approved.

As noted above, there are only 2 doses of immediate release in the EU 2.5 and 5.0 mg. As only 2 doses are licensed personalised dosage titration is difficult.

Figure 11:
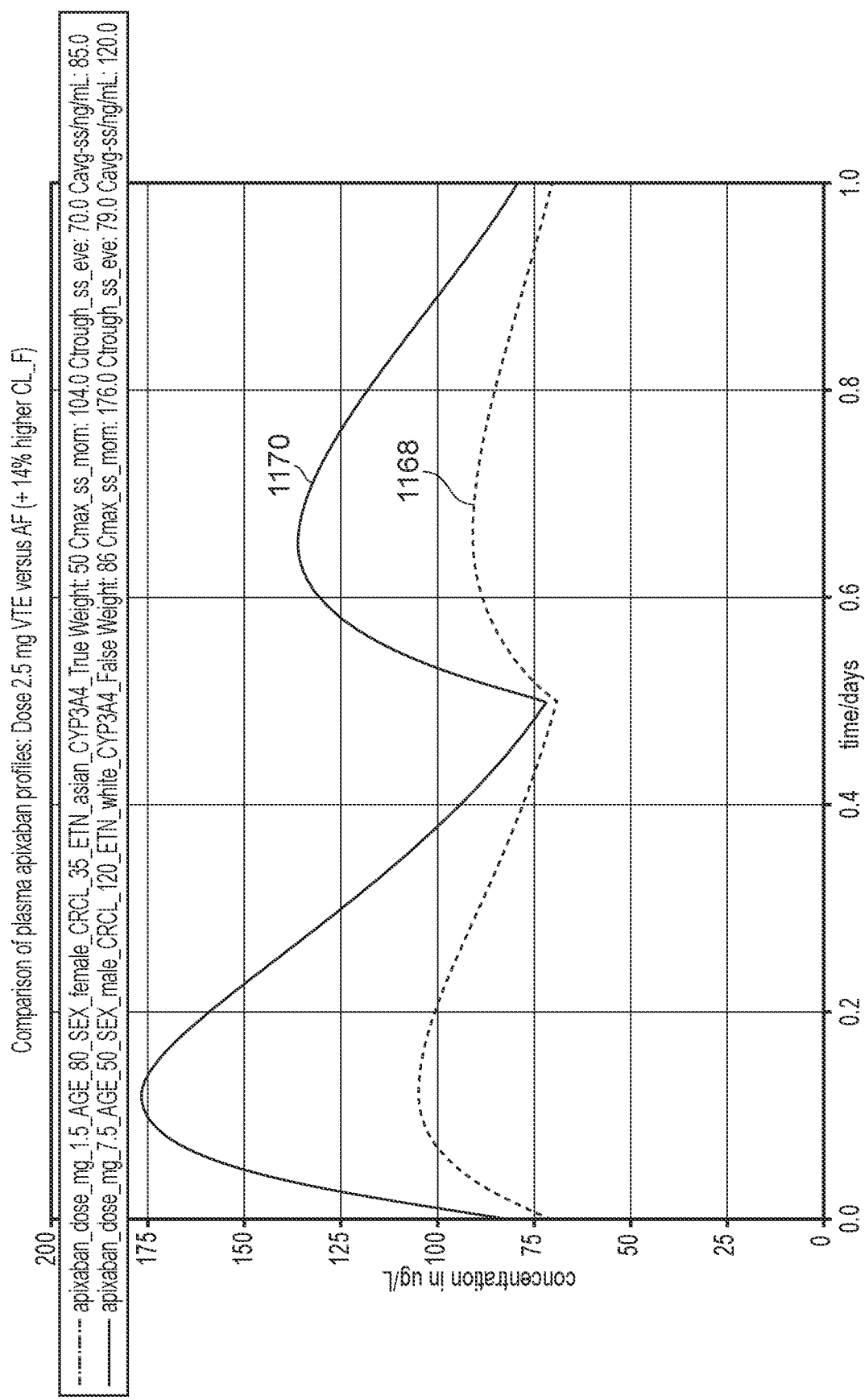
FIG. 11 illustrates the estimated steady-state plasma level time profile for the same two simulated patients of FIG. 4E taking novel dosages to provide ideal trough plasma levels as determined by a plasma level prediction model according to an embodiment of the disclosure.

Thus the need for other doses is apparent such as 0.5 mg, 1 mg, 2.5 mg, 5 mg, 7.5 mg, 10 mg, 15 mg which can provide the right dose for the right patient using the app algorithms described above. FIG. 11 illustrates the estimated steady-state plasma level time profile for the same two simulated patients of FIG. 4E taking novel dosages to provide trough plasma levels in the centre of the optimum window/ITL range. A first plot 1168 for the first subject (80 years old, CrCL=35 ml/min, female, white ethnicity, weight=50 kg, taking CYP3A4 inhibitor) taking a dose of 1.5 mg Apixiban twice daily shows a trough level of 70 mg/ml and an average plasma level of 85 mg/mL. A second plot 1170 for the second subject (50 years old, CrCL=120 ml/min, male, white ethnicity, weight=86 kg, not taking CYP3A4 inhibitor) taking a dose of 7.5 mg Apixiban twice daily shows a trough level of 79 mg/mL and an average plasma level of 120 mg/mL. The Figure illustrates examples of a currently non-available doses (1.5 and 7.5 mg) achieving ideal trough plasma levels. The figure illustrates one example where doses other than those presently available may be most suitable for a given patient. Other examples include where lower doses may be more suitable before and after surgery or where a patient exhibits all the indices for prolonged retention of the drug in the body, or to reflect the changing risk of thrombosis in an individual with time.

The disclosed plasma level prediction models, dosage calculators, digital apps and associated methods can account for other dosage amounts as described above. Indeed, the disclosed systems and methods can perform better when more precise dosage amounts are available.

All of the available doses are immediate release producing peak levels after approximately 3-4 hours when taken without food and 1 hour later after food. Since the mean half-life is only 12 hours, a second dose is required in the evening to achieve stable plasma levels. Multiple dosing can result in poor patient compliance. Therefore, there is a need for the development of sustained release formulations. Sustained release formulations would have the advantage of not only allowing once a day dosing but also reducing the maximum drug plasma level, Cmax, which is associated with bleeding episodes.

The disclosed methods and calculators may also determine a dosage regimen that increases the frequency of dosing to achieve optimal plasma levels without exceeding a threshold value of Cmax. The inventors have realised such a capability is desirable because haemorrhage risk is more related to Cmax in contrast to thrombosis risk which is more related to overall drug exposure and hence Caverage, AUC or blood trough levels. Overall it may be desirable to minimise the Cmax/trough ratio, and avoid Cmax exceeding certain levels. Computing such profiles for particular patients has hitherto not been practically possible, but is enabled by the methods and apparatus disclosed herein.

The half-life of Apixaban is approximately 12 hours and thus twice a day dosing is recommended. However, controlled release formulations may be developed for such purposes, for example using a microgranule formulation (or any other known formulation for controlling solubility and half-life) which would only need to be taken once a day to improve compliance and reduce multiple peaks and troughs of plasma drug levels. Each microgranule may exhibit a controlled release profile and development of multiple doses may be facilitated by altering the number of microgranules in the capsule without having to reformulate and test for each individual dose. It is also envisaged that a reformulation can address the issue of hygroscopicity that prevents the licensed formulation of Apixaban from being placed in dosette boxes or similar in patients requiring such assistance devices.

The disclosed models, calculators, apps and methods can accommodate such changes to dosage form, potentially following clinical trials to refine and validate the plasma level prediction model and/or dosage calculator.

Plasma Level Metric Outputs

Embodiments of the dosage calculation method, particularly those of the digital app implementation, may also process the patient data to determine and optionally output one or more plasma level metrics. The dosage calculation method may comprise determining one or more of: a maximum plasma level (Cmax); Caverage at steady state, a trough plasma level; a ratio of the maximum plasma level to the trough plasma level; a plasma level time profile; an area under the curve of the blood plasma level profile; a ratio of the maximum blood plasma level to the area under the curve of the blood plasma level profile. The dosage calculation method may comprise outputting one or more of these plasma level metrics to the patient or HCP.

As discussed further below (under the "Personalised Target Plasma Level Metrics" section), the maximum plasma level, the trough plasma level and/or the ratio between these may be used to adjust the target plasma level metric to ensure an optimal balance between bleeding risk and thrombosis risk. Outputting these plasma level metrics to a HCP can enable the HCP to manually adjust the target plasma level metric.

In some embodiments, the dosage calculation method may comprise outputting the plasma level time profile or risk levels derived from the plasma level time profile. The plasma level time profile may comprise data similar to that represented in FIG. 4B representing the variation of drug plasma level with time. In such examples, the patient data may include a dosage time at which the patient received a dose of Apixaban. The dosage time can then be used as a start time for the plasma level time profile.

The digital app may use the plasma level time profile to determine and indicate a patient thrombosis risk and/or a patient haemorrhage/bleeding risk according to the plasma time level profile and the dosage time. The digital app may translate circulating drug plasma level to risk based on predetermined plasma level-risk relationships.

Indicating the bleeding risk may comprise indicating to the patient (e.g. via the digital app), times of day at which they are at increased or reduced risk of haemorrhage and thus able to adapt their behaviours accordingly.

In some examples, a HCP portion of the app may output the bleeding risk, the plasma level time profile and/or a circulating drug plasma level (derived from the time profile) to a HCP in advance of an invasive procedure. Such information provided to the HCP can guide timing of procedures and how long a medication should be withheld before a particular invasive procedure, such as surgery, and how soon a procedure can be carried out. In some examples, the digital app may indicate a time that the patient or HCP should wait before undergoing an invasive procedure (or changing medication to a different anticoagulant). The output plasma level metrics can be used to determine if the Apixaban plasma levels are suitable for surgery, for example where an invasive procedure plasma level threshold (cut off) of ~30 ng/ml [10] is thought to be acceptable, aiding the clinical decision. It is recognised that different surgeries carry different risks and the thresholds may be adapted accordingly.

Figure 13A:
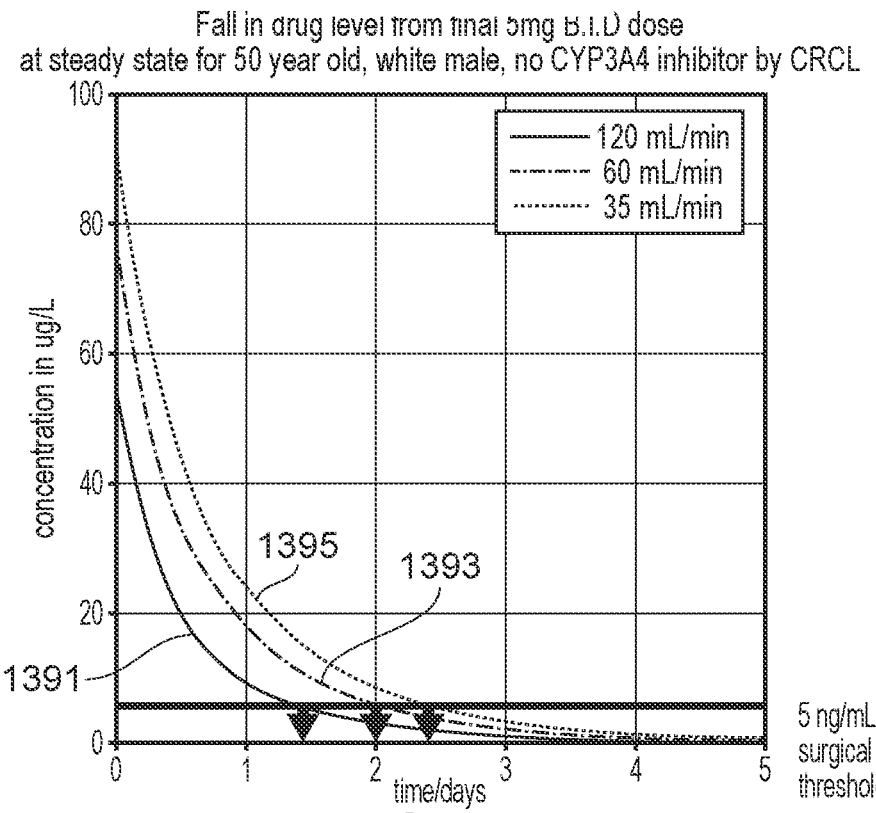
FIGS. 13A and 13B schematically illustrate the determination of procedure wait times according to an embodiment of the present disclosure.
Figure 13B:
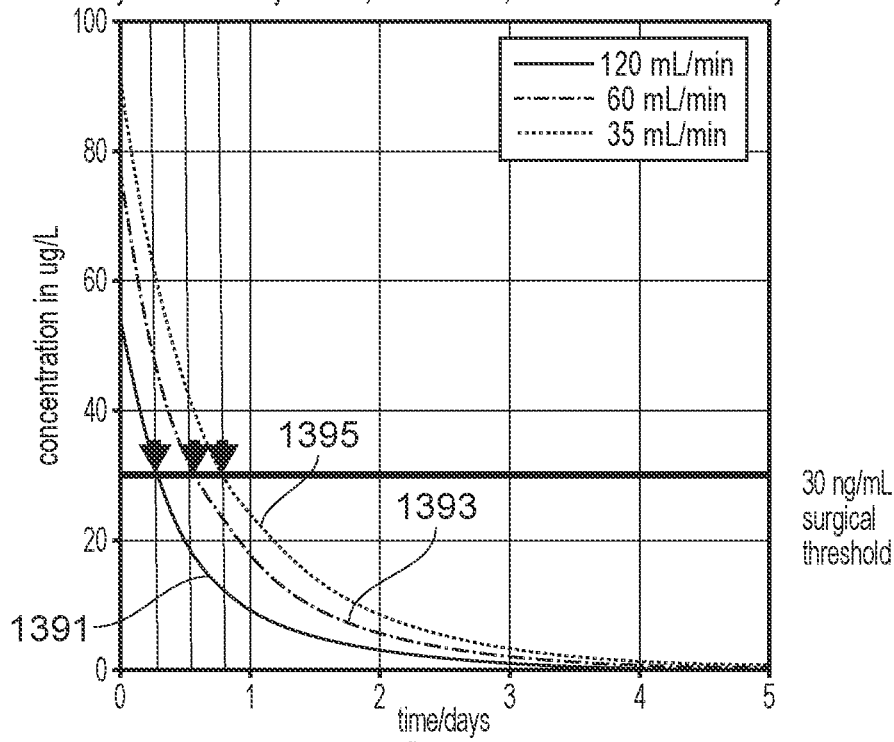

FIGS. 13A and 13B schematically illustrate the determination of procedure wait times according to an embodiment of the present disclosure. The procedure wait time can define a time from the time of the final dosage of Apixaban prior to an invasive procedure until the plasma level has fallen below the invasive procedure plasma level threshold. The invasive procedure plasma level comprises a plasma level deemed safe for the invasive procedure (i.e. Apixaban levels have sufficiently reduced to avoid major haemorrhaging).

The figures illustrate time-dependent plasma level profiles calculated using the second example dosage calculator (i.e. directly using the plasma level prediction model of equations 1-11). The two figures illustrate three time-dependent plasma level profiles: a first plasma level profile 1391 for a first subject with healthy kidney function CrCL=120 mL/min; a second plasma level profile 1393 for a second subject with impaired kidney function CrCL=60 mL/min; and a third plasma level profile 1395 for a third subject with severely impaired kidney function CrCL=30 mL/min. FIG. 13A illustrates an invasive procedure plasma level threshold of 5 ng/ml. Such a low threshold may relate to a major surgery. The procedure wait times for the first to third subjects are 34 hours, 48 hours and 58 hours respectively. FIG. 13B illustrates an invasive procedure plasma level threshold of 30 ng/mL. The higher threshold may relate to less invasive surgery. The procedure wait times for the first to third subjects are 6 hours, 13 hours and 18 hours respectively.

In some examples, the patient data includes a final drug dosage prior to drug withdrawal in advance of an invasive procedure and the app/method processes the final drug dosage with the dosage calculator to determine a procedure wait time for the plasma level to fall below an invasive procedure plasma level threshold. The final drug dosage may include a dosage amount and/or a dosage time. In some examples, this procedure wait time calculation may be performed independently of any dosage calculation and may be performed for any DOAC.

Figure 14:
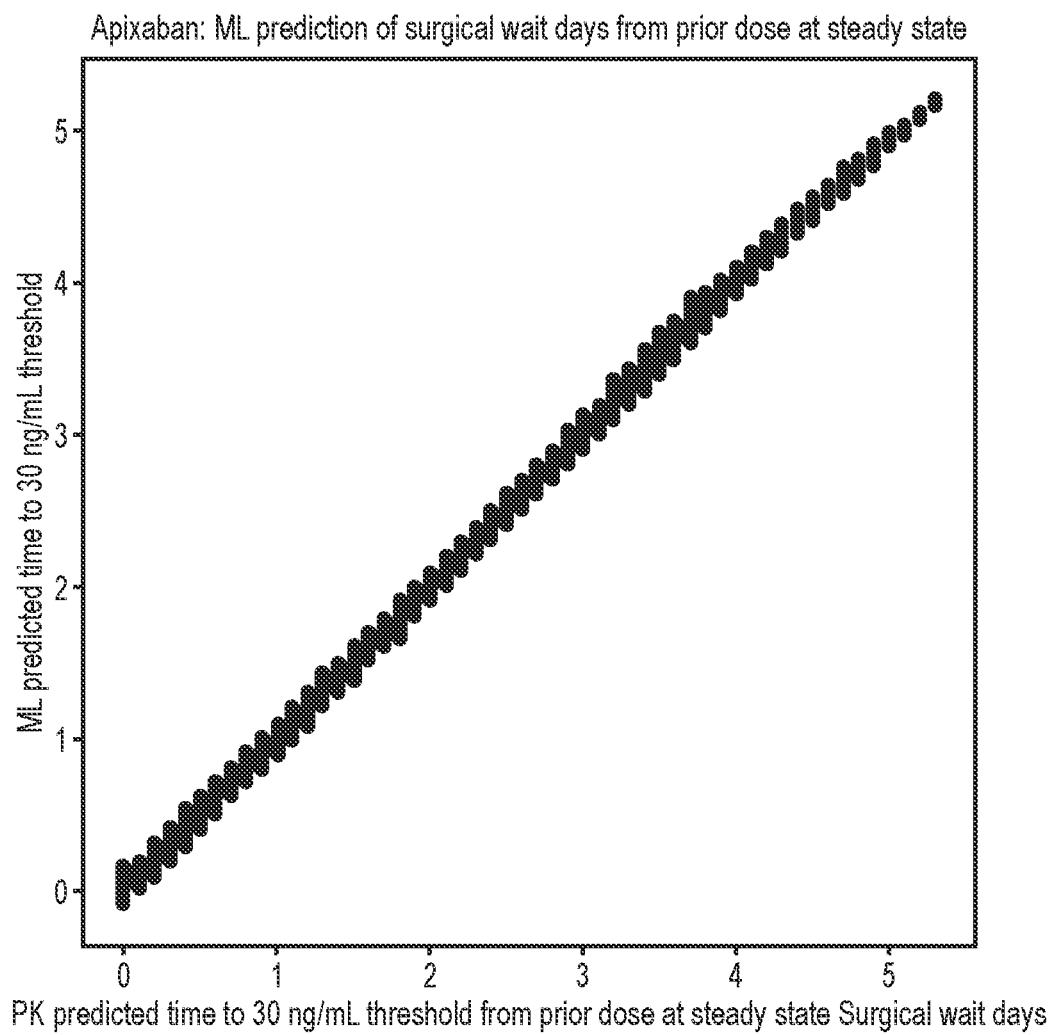
FIG. 14 plots the predicted procedure wait time calculated with a machine learning dosage calculator versus the predicted procedure wait time calculated with a plasma level prediction model according to an embodiment of the present disclosure.

In some examples, a ML dosage calculator may be used to determine the procedure wait time. The ML dosage calculator may be trained using simulated population data comprising simulated patient data (as described above) and simulated procedure wait times calculated with the plasma level prediction model/second dosage calculator. The ML dosage calculator may be trained for a specific invasive procedure plasma level threshold or may be trained for a range of invasive procedure plasma level thresholds. The trained ML dosage calculator may: receive patient data including a final drug dosage; and process the patient data to determine a procedure wait time for the plasma level to fall below an invasive procedure plasma level threshold. FIG. 14 plots the predicted procedure wait time calculated with a ML model versus the predicted procedure wait time calculated with the plasma level prediction model. The figure illustrates excellent agreement between the two approaches. A ML based dosage calculator for predicting surgical wait times realises the same advantages as the ML based dosage calculator described above, namely the ability to deploy the calculator at scale for rapid calculations because there is no requirement to process the differential equations (1-4) of the plasma level prediction model.

In some examples, a patient facing portion of the digital app may indicate the thrombosis risk including advising isolated periods of thromboprophylaxis for events where they are at higher risk of a further thrombosis, for example, surgery or flights of longer than four hours duration, after the patient has completed regular anticoagulation for the original clot. The app could advise on when to increase back to therapeutic anticoagulation from prophylactic after pausing anticoagulation for a planned procedure. This latter aspect could be either presented in a patient facing app, and/or a clinician facing app.

In some examples, the digital app may receive patient data from other objective monitoring systems. The digital app may receive activity data, e.g. from wearable devices, to monitor activity levels and impute associated risk elevation or reduction. Increased activity confers lower risk of stroke, but must not exceed a level that bleeding risk is unacceptably elevated. The digital app may also receive blood pressure data from a blood pressure monitoring device. Blood pressure is linked with the probability of stroke, including haemorrhagic stroke. The digital app may adjust or scale the bleeding risk or thrombosis risk based on the blood pressure data and/or the activity data. Incorporating home blood pressure monitoring data into the patient data and providing it to the HCP may also be useful to help the HCP decide if additional treatment is necessary, something that is not routinely undertaken in patients receiving DOACs.

Personalised Target Plasma Level Metrics

The tendency to clot can be influenced by a variety of patient parameters that vary with time and between individuals, such as those already described above and in addition, hydration state, infection, inflammation, menstruation, blood pressure and the rate of blood flow through blood vessels. Sluggish blood flow can be seen with prolonged immobility, and in particular after surgery. Increased risk of haemorrhage can occur if there is trauma or a medical procedure involving penetration of a needle, or surgery. As already described, blood vessel walls can become weaker as a result of ageing and in particular deposition of amyloid as occurs in the brain, or from inflammatory processes or drugs such as steroids or antidepressants. The beginnings of clot formation may occur as part of the normal range of physiology, but anticoagulant properties of the coagulation cascade prevent extension.

The inventors have realised that the process of clot formation, or thrombosis, takes place over a longer time course than the process of haemorrhage. The balance between thrombosis tendency and haemorrhage tendency will vary between individuals based on their particular body state. The tendency can be shifted by dosing of DOACs. The longer process of thrombus formation is more closely related to the total exposure to the DOAC, whereas the haemorrhage tendency is more related to the maximal drug concentration. Therefore, consideration of both of these parameters and the ratio thereof offers a route to a more personalised approach to anticoagulation to achieve the best risk benefit profile. For example, one approach may be to minimise the ratio of the maximum plasma level, Cmax, to the area under the plasma level time profile. As noted above, current formulations can only suppress Cmax by prescribing multiple doses per day which brings its own problems of compliance. The solution of a controlled release product that can be used once daily while desirable is not yet available.

Disrupting the above balance of risk, and exacerbating incorrect dosing of anticoagulants, is an asymmetry in prescribing tendency amongst HCPs reflecting the psychological desire for blame avoidance. HCPs may perceive the occurrence of a thrombosis which then may lead to an embolism as less blameworthy than occurrence of a haemorrhage (omission vs commission). As a consequence HCPs may tend towards under dosing to avoid the risk of a potential overdose, even though at a population level this leads to worse outcomes. This reflects a psychological flaw rather than rational prescribing.

Embodiments of the dosage calculation method, particularly those of the digital app implementation, may account for individual clotting and bleeding risk factors by determining the target plasma level metric as a personalised plasma level metric. In some examples, the target plasma level metric may comprise a trough plasma corresponding to the ITL. The personalised plasma level metric may comprise an adjustment to the ITL. As discussed below, the personalised plasma level metric may also include a ratio of the maximum plasma level, Cmax, to the area under the plasma level time profile being less than a bleeding risk threshold.

In examples employing personalised target plasma level metrics, the patient data may include one or more target dependent patient parameters. The target dependent patient parameters may comprise one or more of: reported side effects (see "side effect monitoring" below); a patient thrombosis history; a patient haemorrhage history; a patient cancer history; a patient stroke history; a patient liver function metric; a patient heart function metric; a patient brain state; a patient smoking history; a patient alcohol history; a patient blood pressure; a patient mobility state; a patient menstruation state; a patient inflammation state; a patient infection state; a patient co-medication; a blood clotting metric; and a patient hydration state. The dosage calculation method may determine the personalised plasma level metric based on one or more of the target dependent patient parameters. The target dependent patient parameters may be monitored on an ongoing or regular basis and personalised target plasma level metrics may be refined on an ongoing basis as part of the ongoing treatment management discussed below.

In some examples, the method may determine personalised adjustments to the target plasma level metric based on specific calculations relating to one or more specific target dependent patient parameters, particularly those indicating a time-limited risk resulting from a risk event (fall, surgery etc). Other target dependent patient parameters that result in bleeding or haemorrhage risk may be chronic in nature or lifestyle dependent, such as a genetic clotting disorder, alcoholism etc.

In some examples, the method may output the personalised adjustments to the patient or HCP. For example, the method may indicate a personalised ideal therapeutic trough level for an individual.

Risk Events

In some examples, the dosage calculation method may comprise determining the personalised plasma level metric based on a time since a bleeding risk event and/or a haemorrhage risk event. For example, the method may comprise applying a maximum adjustment to the nominal target plasma level metric immediately following the risk event and tapering the adjustment periodically back towards the nominal target plasma level metric as the time since the event increases. The method may indicate new dosage regimens with each variation of the adjustment.

For example, immediately following surgery, a patient may be at high risk of bleeding for the first 48 hours before the risk drips rapidly. Anticoagulant may be avoided during this period, except for high thrombosis risk patients. Following this initial period, the patient may be most at risk of thrombosis due to inflammation associated with healing and reduced mobility. At this stage, the method may determine a personalised target plasma level metric as an average plasma level Caverage at the upper end of the ITL or above the ITL, e.g. 125 ng/ml. The dosage calculation method may comprise determining and indicating a dosage for administering to the patient that can provide the personalised target plasma level metric. Following a fixed period after the surgery, e.g. a number of days, the dosage calculation method may comprise reducing the personalised target Caverage level to ~100 ng/ml and determining and outputting the dosage for administering accordingly. This may continue until the personalised target level metric is reduced to the ITL.

Other thrombosis risk events include: a thrombosis; one or more episodes of atrial fibrillation; dehydration; chemotherapy; an injury; a surgical procedure, particularly large joint orthopaedic procedures such as hip replacements; indwelling central venous catheters such as Hickman lines. Bleeding risk events include: a haemorrhagic stroke; an injury; a surgical procedure; needle penetration; or a patient fall.

A number of events result in both a bleeding risk and a thrombosis risk (e.g. falls and surgery). For such examples, the method may comprise determining the personalised plasma level metric as a ratio of Cmax to the area under the plasma level time profile being less than a bleeding risk threshold. This may be in combination with maintaining the plasma level within the ITL. In such examples, the method may comprise determining and indicating a dosage regimen comprising a controlled release formulation or a dosage frequency of more than twice a day, for example 8 hourly or 6 hourly, combined with a lower dosage amount, for example 2.5 mg or less if suitable dosage forms are available. Although, a higher dosage frequency can reduce compliance, it can be properly managed for carefully managed patients e.g. cancer patients, and in care settings for example post-surgery or in a nursing home. As mentioned above cancer patients can be at risk of both thrombosis and haemorrhage. Therefore, the method may also comprise determining similar personalised plasma level metrics (ratio and/or trough level) and dosage regimens for cancer patients. Furthermore, some patients may have a chronic bleeding or thrombosis risk and experience a thrombosis risk event or bleeding risk event. The method may also account for such dual risk by personalising the ratio and drug dosage regimen in a similar manner.

Chronic or Lifestyle Related Risk Parameters

A patient fall may also provide an indication of a risk of further falls. There is a challenge in judging when the bleeding risk from a fall outweighs benefits of anticoagulation. A rough guide is if there are more than nine falls per year, anticoagulation may be contraindicated, but this depends on the nature of the fall. The dosage calculation method may reduce a target plasma level or the ratio of Cmax to the area under the time profile based on the frequency and/or timing of falls as indicated by the patient fall history. Data from devices that measure fall propensity may input into the system and the patient facing app may offer tailored advice as to risks from falls, or other activities, mitigating actions and when, in relation to the timing of medication taking, their risks are highest and lowest.

The risks of bleeding are in part related to age. Reasons are not fully understood, but may in particular relate to the alterations in endothelium with age, including through changes in collagen. The dosage calculation method may reduce a target plasma level or the ratio of Cmax to the area under the time profile based on patient age.

An additional problem for females relates to menstruation and contraception. Oestrogen increases the rate of thrombosis, so oestrogen based pills are usually stopped (As an aside, the menstrual cycle can also affect INR readings making Warfarin a difficult drug for menstruating patients). A patient may then have heavy periods and become anaemic and then have blood transfusions. Some may inadvertently fall pregnant. Optimal management is missed for the majority. Most do not know if their periods are abnormal. Data on menstruation patterns may input into the system and the patient facing app may offer tailored advice as to contraception and menstruation, e.g. advise appropriate treatment for heavy menstrual bleeding. The app could also alert the HCP to the issue.

Other target dependent patient parameters that can increase bleeding risk and therefore may require a reduction in target plasma level and/or the ratio of Cmax to the area under the time profile include: high patient blood pressure (haemorrhagic stroke risk), poor liver function, the presence of amyloid in the brain, poor renal function, high alcohol consumption and an indication of aspirin, clopidogrel, NSAIDS, steroids, anti-depressants or any other medication that can result in heightened bleeding risk. In some examples, the dosage calculation method may determine a bleeding risk score based on the presence, timing, and/or severity of a bleeding risk event and one or more of the aforementioned bleeding risk factors. The dosage calculation method may use the Hasbled score to determine the bleeding risk score.

Alcohol intake can also increase AF and dysthymias potentially increasing the chance of strokes and thrombosis.

The dosage calculation method may determine a personalised target plasma level metric by decreasing the target trough plasma level if the bleeding risk score exceeds a bleeding risk threshold.

Other target dependent patient parameters that can increase thrombosis risk and therefore may require an increase in target trough plasma level include: genetic profile; active cancer or inflammatory state; and patient hydration. In some examples, the dosage calculation method may determine a thrombosis risk score based on the presence, timing, and/or severity of a thrombosis risk event and one or more of the aforementioned thrombosis risk parameters.

The dosage calculation method may determine a personalised target plasma level metric by increasing the target trough plasma level if the thrombosis risk score exceeds a thrombosis risk threshold.

In some examples, the dosage calculation method may receive the bleeding risk score and/or the thrombosis risk score via data entry from a HCP.

The dosage calculation method may determine a personalised target plasma level metric as a ratio of Cmax to the area under the plasma level time profile being less than a bleeding risk threshold if the thrombosis risk event exceeds a thrombosis risk threshold and the bleeding risk score exceeds a bleeding risk threshold.

In some examples, the method may comprises assigning patients to one of a plurality of sub-groups. Each sub-group may correspond to one or more of the target dependent patient parameters described above. The method may comprise assigning the patient based on time since a risk event, and/or the presence of a particular patient risk factor. Each sub-group may have a corresponding personalised target plasma level metric.

Ongoing Treatment Management

As the patient's state changes, so does their pharmacokinetics and pharmacodynamics, with the result that they can become under dosed or overdosed.

Ideally, the patient should be reviewed at least once per year and for high risk patients potentially every 3 to 6 months, or more frequent follow-ups for particularly high-risk patients (e.g. those with renal failure, where signs of bleeding are occurring in preparation for surgery, when the subject is taking drugs with interactions on absorption or where the chance of stroke is particularly high).

A comprehensive DOAC monitoring approach may include one or more of the following items assessed at each follow-up:

1. Current health status
    e.g. a measure of blood pressure and blood sample to check for new anaemia, liver and kidney function.
2. Lifestyle assessment, including nature of sports.
3. Risks of falls.
4. Personalised risk of haemorrhage and thrombosis.
5. Adherence and cost.
6. Bleeding/thromboembolic events.
7. Adverse effects.
8. Complete medication review for drug interactions.
9. Reassessment of appropriateness of therapy.
10. Repeat warranted laboratory parameters.
11. Continuing follow-up appointments for patients Embodiments of the digital app and associated methods may include providing a HCP with a summary of key patient data parameters that have been tracked during the treatment period. The digital app may track any of the patient data parameters described herein for presentation to a HCP. The patient data parameters may be tracked via manual data entry from a patient, HCP or clinic, from clinical records or any other input method. Parameters which may be tracked include, amongst others, age, weight, renal function, liver function, bleeding tendencies, any new thrombotic events and falls risks.

Embodiments of the digital app and associated methods may include tracking the aforementioned patient data parameters as updated patient data (for example on a regular basis (daily, weekly, monthly)), processing the updated patient data parameters to determine an updated dosage for administering to the patient; and indicating the updated dosage. For example, changes to the patient data underpinning the plasma level prediction model (such as kidney function or medication) may result in a different calculated dosage to obtain the target plasma level metric. As a further example, changes to the patient data that indicate an increase in bleeding and/or thrombosis risk may result in a personalisation of the target plasma level metric (as described in the preceding section), thereby resulting in a change to the recommended dosage for administering to the patient. Indicating the updated dosage may comprise: indicating the updated dosage to a HCP at a regular review meeting; and/or indicating the updated dosage to a HCP or other healthcare professional (pharmacist, nurse etc) via an alert if a change in the updated dosage exceeds an alert threshold.

Embodiments of the digital app and associated methods may include tracking or monitoring patient data comprising side effects such as excessive bleeding, GI dysfunction, vomiting, skin rashes etc, as well as the behavioural pattern of the patient (and others listed in side effect monitoring below). The patient data may be provided to the HCP as part of the health care review or alerted if significant, e.g. hemorrhage.

By tracking the patient data, underlying changes to a patient's physiology with time, age, disease progression or through drug or lifestyle or other environmental factors can be periodically evaluated to maintain personal calibration of the dose yielding ideal therapeutic level for that patient.

Blood Coagulation Test Monitoring

Ideally an ongoing monitoring program should include measuring drug trough plasma levels. However the measurement of plasma drug concentrations drug levels in both hospitals and the Home Care Provider setting is rare, costly and seldom undertaken.

Specific quantitative measures exist for Apixaban such as plasma Apixaban drug concentration, as well as coagulation measurements such as anti-factor Xa levels, modified prothrombin time (mPTT) or activated partial prothrombin time (aPTT) to directly assess anticoagulation effects. Currently the activated prothrombin time are used in high risk patients and in particular to indicate when the bleeding risk is sufficiently low to allow surgery, with a typical threshold being a blood level of 30 ng/ml. One issue is that these measures have not been shown to directly relate to clinical outcome and agreed standardized therapeutic ranges have not been established. In addition these more specific tests are not always available to every health care provider.

Other coagulation tests include chromogenic assay (ECA) and the INR test, the latter being the standard test for warfarin and vitamin K antagonists (VKA) compounds.

Unlike with the VKA anticoagulants these tests can relate directly in time to the circulating Apixaban plasma levels due to the lack of PKPD hysteresis.

Frost [3] has related some of these measures to circulating plasma levels of Apixaban (Cp) at steady state as shown in the following equations:

$$\text{For INR: INR} = 1.137 + 0.0011 * Cp$$

$$\text{For } a\text{PTT: } a\text{PTT} = 30.60 + 10.41/[1 + (301.5/Cp) * 1.2)]$$

$$\text{For } m\text{PTT: } m\text{PTT} = 48.92 + 0.1993 * Cp$$

In addition, new assays are in development that may enable better computation of Apixaban drug plasma levels.

Embodiments of the digital app or associated methods may include receiving patient data comprising a patient coagulation metric (also referred to herein as a patient clotting metric) from a blood coagulation test result. The patient clotting metric may comprise a drug plasma level (also referred to as drug concentration). The patient clotting metric may comprise any of the above blood clotting metrics and the embodiments may comprise calculating a measured drug plasma level based on the blood clotting metric. In some examples, the embodiments include calibrating the dosage calculator and/or plasma level prediction model by comparing the measured drug plasma level to a corresponding plasma level metric calculated by the dosage calculator. Following calibration, embodiments may comprise processing the patient data with the calibrated dosage calculator to determine an updated dosage of Apixaban for administering to the patient.

A challenge with measuring drug or clotting level via a blood test is relating this to a time of administration and therefore a trough level is typically taken. This can be logistically challenging compared to taking a sample at any time point. Embodiments of the present disclosure allow for individualised calculation of clotting parameters and drug profile by recording the time of medication and the time of blood sample collection (which may be any time) as patient data. Embodiments of the digital app and associated methods may include: receiving a time of drug administration, a time of blood sample and a measured drug plasma level as patient data; and combining the measured drug plasma level, the time of drug administration, and the time of the blood sample with the plasma level time profile estimated by the dosage calculator to adapt the measured drug plasma level to a measurement-derived maximum plasma level, Cmax, a measurement-derived average plasma level, Caverage, or a measurement-derived trough plasma level, Ctrough. In other words, the digital app and associated methods can convert a blood test taken at any time point to any measurement-derived plasma level.

Embodiments of the digital app and associated methods may also calibrate the plasma level prediction model and/or dosage calculator based on the measured drug plasma level or clotting metric. Embodiments of the digital app and associated methods may include: receiving a time of drug administration and a time of blood sample as patient data; estimating a drug plasma concentration at the time of the blood sample using the dosage calculator based on the dosage amount and the time of drug administration; and calibrating the plasma level prediction model and/or the dosage calculator based on the difference between the estimated drug plasma concentration and the measured drug plasma concentration. In some examples, embodiments may comprise calibrating the plasma level prediction model and or dosage calculator based on a difference between the maximum plasma level estimated by the dosage calculator and the measurement-derived maximum plasma level and/or a difference between the trough plasma level estimated by the dosage calculator and the measurement-derived trough plasma level. In this way, the dosage can be adjusted to obtain a corrected ITL. Using both trough and maximum levels of coagulation, the best dose for a particular individual can be recommended.

In examples where the digital app and associated methods are used for patients having a high bleeding and clotting risks (e.g. surgery patients, cancer patients, elderly patients, patients prone to falls), regular blood test monitoring may be employed to ensure accuracy of the dosage calculator and/or underlying plasma level prediction model. The methods may comprise updating the dosage calculator, the plasma level prediction model, the personalised target plasma level metrics (e.g. ratio, average or trough level as described in previous section), and/or the indicated dosage for administering to the patient, based on the calculated or measured drug plasma level.

The availability of coagulation test data also allows for personal calibration of the dose prediction model. The plasma level prediction model and dosage calculator can predict circulating drug for an average patient at any time following drug intake. This would lead to a predicted coagulation test result. By comparing the actual coagulation test result to the predicted, the dose prediction model can be proportionately adjusted for the individual characteristics or vice versa.

If the dose response is personally calibrated with confidence then dosing may be adjusted to accommodate acute or long term changes in patient data, such as adjustment to accommodate temporary or long term anti platelet therapy, for example given following coronary artery stenting (e.g. via personalised target plasma level metrics as described above). Drugs like aspirin or NSAIDs may also be taken inadvertently by a patient for a headache or pain, the patient not realising it has a potential additive effect with Apixaban on the risk of a major bleed.

In some examples, the digital app and associated methods may be used in conjunction with a low cost home test for plasma Apixaban level. Combining the app and methods with such tests may calibrate the model and optimise/minimise the frequency of future test requirements. In some examples, it may be sufficient to improve prediction by undertaking just one such assessment. Measurement of the drug level at home may be easier and lower cost than clinic tests and potentially be undertaken at a convenient time during treatment (e.g. just prior to a dose, i.e. at trough level), rather than at an arbitrary time during the day or in an emergency period before surgery Personal calibration can be particularly advantageous for Apixaban because of the low absorption rate and resulting inter-subject variability in absorption (and resulting plasma level). Individual absorption variability is difficult to model as it can arise from a range of event scenarios (e.g. is the drug taken with food, hydration level, gut metabolism etc). Calibrating the dosage calculator with a blood test can advantageously account for the absorption variability between subjects. However, it will be appreciated that personal calibration via blood tests is optional. In many examples (e.g. lower risk patients), the HCP may rely on the dosage recommendation and/or plasma level metrics provided by the app and associated methods disclosed herein.

Other patient data parameters that may be monitored by the app or associated methods may include signs and symptoms of bleeding, complete blood count, and a comprehensive metabolic panel specifically evaluating liver function tests, albumin, total bilirubin, and serum creatinine.

Side Effect Monitoring

As noted above, the app and associated methods may comprise receiving patient data as self-reported side effects. The digital app and associated methods may monitor side effects of Apixaban, including those that can occur when the dosage is too high (see table 4), using suitable questions. GI tract disturbances and bleeding in particular may be closely monitored. The digital app and associated methods may take a number of actions in response to detecting a side-effect above a respective sensitivity level, including: alerting a clinician; advising the patient to make a medical appointment; recommending a blood test for calibration (as described above); adjusting a bleeding risk level; adjusting a thrombosis risk level; adjusting a personalised target plasma level metric; recalculating the dosage for administering to the patient based on the adjusted bleeding risk level, adjusted thrombosis risk level and/or adjusted personalised target plasma level metric; and indicating an updated dosage for administering to the patient to the clinician or patient. By monitoring and acting on side effects the app and methods can provide important feedback to the HCP on the need to obtain measures of anticoagulation (blood tests) and advise on suitable dosage change for that particular patient. The principle side effect of Apixaban relates to increased bleeding tendency, with undesired haemorrhage, sometimes fatal.

TABLE 4

Common Side Effects of Apixaban

Reduction in red blood cells
Reduction in the number of platelets

TABLE 4-continued

Common Side Effects of Apixaban

Figure 12:
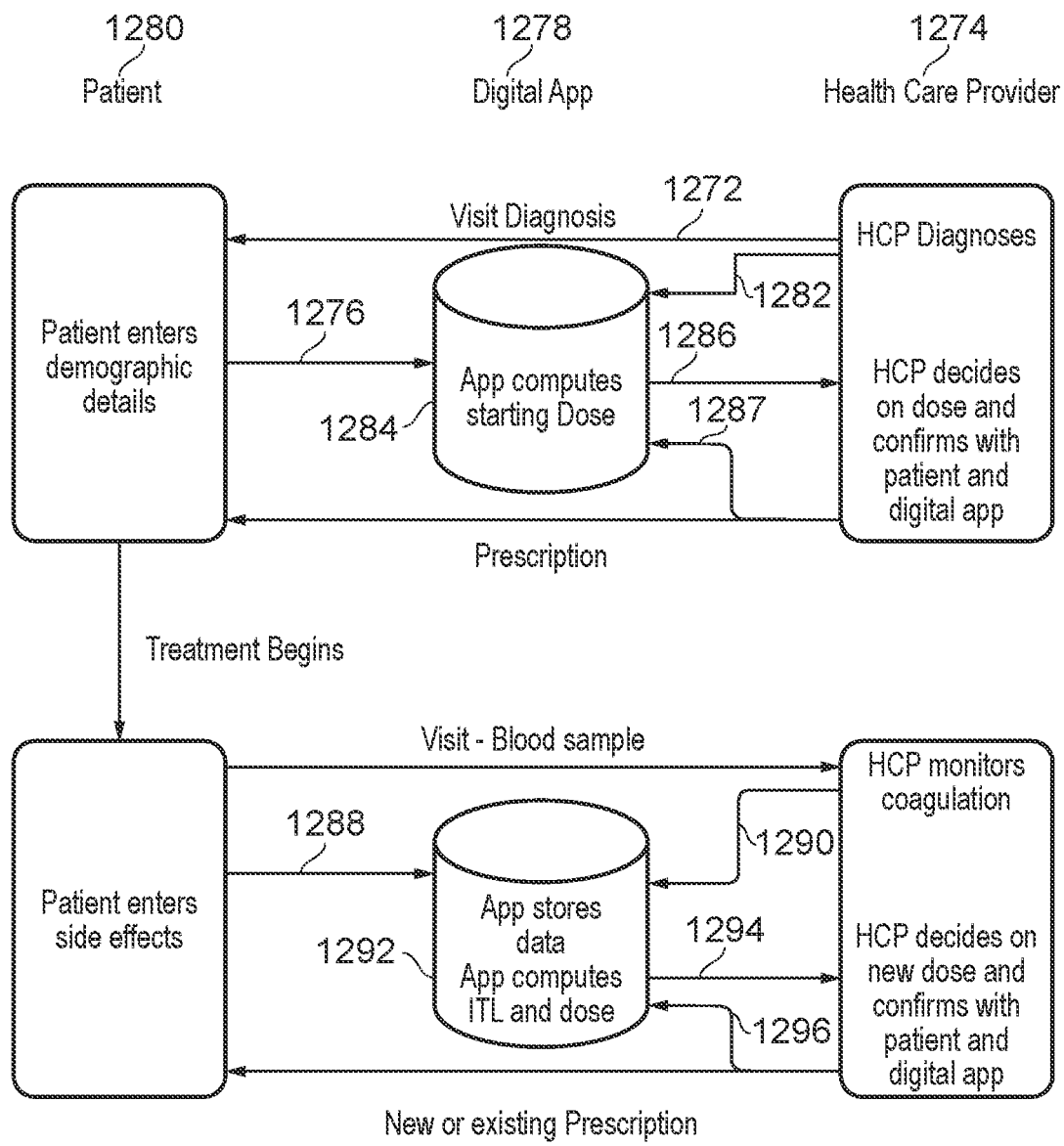
FIG. 12 illustrates an example patient monitoring process according to an embodiment of the present disclosure.

Skin Rash with itch bumps and allergic reactions
Haematoma formation
Nosebleed
Gastric Reflux
Vomiting
Feeling Sick
Frequent loose or liquid bowels
Indegestion
Hair Loss
Increased liver enzymes FIG. 12 illustrates an example patient monitoring process according to an embodiment of the present disclosure.

Following a diagnosis 1272 by a health care provider (HCP) 1274, for example a HCP, a first step of the method comprises receiving 1276, at the digital app 1278, patient data comprising demographic details entered by the patient 1280. The method may also comprise receiving 1282, at the digital app, patient data from the HCP 1274 (e.g. via manual data entry or clinical records etc).

Following receipt of the patient data, the method proceeds to processing the patient data 1284 using the dosage calculator to determine a starting dosage regimen for administering to the patient 1280. Following calculation of the starting dosage regimen, the method comprises indicating the dosage regimen 1286 to the HCP 1274. The HCP 1274 may consider the starting dosage regimen calculated by the app 1278 and provide an initial prescription to the patient 1280. The prescription may be provided 1287 to the digital app 1278 as patient data.

The patient 1280 begins treatment. During treatment the method comprises receiving updated patient data 1288 from the patient 1280, such as side effects or events, and receiving updated patient data 1290 from the HCP following physiological tests such as blood test results comprising blood clotting metrics, drug plasma levels and/or CrCL. The method proceeds to process the updated patient data 1292 to determine an updated dosage for administering to the patient. Processing the updated patient data 1292 may comprise calibrating the plasma level prediction model and/or the dosage calculator based on the measured clotting metric or drug plasma level as described above. Processing the updated patient data 1292 may comprise calculating an updated dosage regimen based on a significant change in a patient data parameter driving the calculator, such as a change in CrCL. Processing the updated patient data 1292 may also comprise personalising the target plasma level metric and calculating an updated dosage regimen as described above. The method proceeds to indicating 1294 the updated dosage regimen to the HCP 1274.

The HCP may consider the updated dosage regimen calculated by the app 1278 and provide an updated prescription to the patient 1280. The updated prescription may be provided 1296 to the digital app 1278 as further updated patient data. The lower loop illustrated on the Figure may be repeated as treatment progresses and optionally as the patient makes further or regular visits to the HCP 1274 e.g. for further blood tests.

Patient Instruction and Education

The digital app and associated methods may comprise providing instruction, guidance and education to the patient to support them with their ongoing Apixaban medication. Due to a lack of ongoing review at present, many patients can feel uncertain in relation to their medication which can lead to poor compliance. For example, the consequences of a thrombosis and a DOAC prescription for the patient extends well beyond the direct effects. Patients live with lots of fear and do not know what to do if a further bleed happens. There are two phases to management of venous thromboembolism, for example the active phase and the preventative phase. In the first phase, the aim is to stop clot extension and early recurrence. This lasts one month, perhaps extending in some to 3 months. After this, there is more flexibility in treatment. There is also limited patient understanding of how to take their medication, with many not realising that they need to request a repeat prescription, interpreting their hospital script as all that is required, like for a course of antibiotics. Some may overlook a requirement for certain medications to be taken with food.

Many patients do not know what to do if they develop a further clot and wrongly assume that they should carry out preventative actions, for example with a clot in their leg, moving the leg around, whereas they should do the opposite, keeping the leg elevated and immobile. Many patients have local complications from a thrombosed vein, with a post phlebitic limb very common. This is often badly managed. The nature and timing of how to wear compression stockings and bandages is not known by most. For patients who have had pulmonary emboli, many misinterpret subsequent chest pain and shortness of breath. If benign causes are misinterpreted, this leads to anxiety and exercise avoidance, with consequent deconditioning and increased future risk of cardiopulmonary events.

Similar concerns and uncertainties around a Apixaban prescription may be experienced by patients taking the drug for prophylaxis purposes, such as patients with AF.

The fact that DOACs aren't monitored in the way that warfarin is with a warfarin clinic means there is limited opportunity for education. Overall, it is estimated that 20 to 25% of patients are not taking their originally prescribed dose.

Therefore, as outlined below, the methods and apparatus of the disclosure are intended to provide patient instruction, guidance and education to support patients with their medication thereby improving trust and compliance.

Instructing Dose Administration

Embodiments of the digital app and associated methods may comprise indicating the dosage to the patient via a patient device. The app may indicate the dosage amount to the patient and may at the same time provide information on how and when to take the medication in relation to food, how to address missed dosing and/or if there are issues with taking other drugs. Taking DOACs with food can slow the absorption of the drug by up to 1 hour and the app may instruct the patient accordingly. Compliance is a particular issue with Apixaban and anticoagulants since failure to take a dose can lead to a reduction in the activity. The digital app can reinforce the need to take the medication on a regular basis according to HCP recommendations, through the use of visual, audio and/or tactile prompts, alerts, alarms, reminders and other alert mechanisms from the patient device. For missed doses, the app and associated methods may calculate a new schedule of dosing and/or adjusted dosage amounts (up or down) for a temporary period using the dosage calculator and the target plasma level metric. The app and associated methods may comprise: receiving a new candidate co-medication (from a HCP or patient), comparing the co-medication against a reference co-medication list; and indicating a co-medication instruction. The co-medication instruction may comprise: a revised dosage for Apixaban, an instruction not to take the co-medication; and/or an instruction to consult the HCP.

Side Effect Guidance

As noted above, the app and associated methods may comprise receiving patient data as self-reported side effects. The digital app and associated methods may provide guidance to the patient on the reported side-effects or any other side-effects to allay patient concern. As noted above, the app may alert the patient that they should seek medical care in the case of severe side-effects.

Lifestyle and Risk Guidance

The digital app and associated methods may also incorporate and deliver a comprehensive education program with advice on the self-monitoring of side effects (as described above), messaging relating to precautions to avoid the chance of stroke and lifestyle modification improvements, such as smoking cessation, reduction in alcohol consumption, journey durations and habits, and hydration status. As noted above in the outputs section, the app and methods may determine periods of bleeding risk and/or thrombosis risk based on the plasma level time profile and suggest timing of risk activities (sport, long journeys etc) relative to the medication time and maximum plasma level, Cmax, as indicated by the plasma level time profile. In this way, the app and methods can minimise the risk of thrombosis and haemorrhage while enabling the patient to maintain a quality of life. As also noted above, the app and methods, may calculate and indicate an adjusted dose in advance and following high risk procedures (e.g. surgery and long journeys).

The education advice may include instructions on management of a phlebitic limb, including duration of elevation, type of bandage or stocking and application procedure, with tracking of any unwanted consequences and management thereof.

The app and methods may also advise on risks of various activities, in particular contact sports and those with higher risks of falls such as skiing. The app and methods may provide individualised risks for informed patient decisions. For example, the app may advise on strategies to decrease risk during long journeys.

The app and methods may provide advice on patients regarding decrease in haemorrhage risk from lifestyle changes, including improving balance to prevent falls and type of exercise, whilst still ensuring optimal quality of life which could be impacted if activities are curtailed too much.

The app and methods may track respiratory symptoms in patients who have had a pulmonary embolism to help identify whether chest pain and shortness of breath is merely residual effects of the original embolus or is a new cause for concern. The prospective tracking overcomes the problems of patient memory.

For females, the app and methods may advise on contraception and also management of heavier periods from the anticoagulant. The app and methods may incorporate bleeding scores to help determine whether periods are abnormal and warrant additional investigation, to pick up, for example, a new cancer.

For patients who have falls, the app and methods may track number of falls and their type to help with risk management.

Patient Example

NB is a 84 year white old male, weight 88 kg, CrCL 83 mL/min, with AF. NB has dementia and suffers from frequent falls. NB's general practitioner and NB's hospital clinician were unable to agree on a correct dosage of Apixaban for NB.

Figure 15:
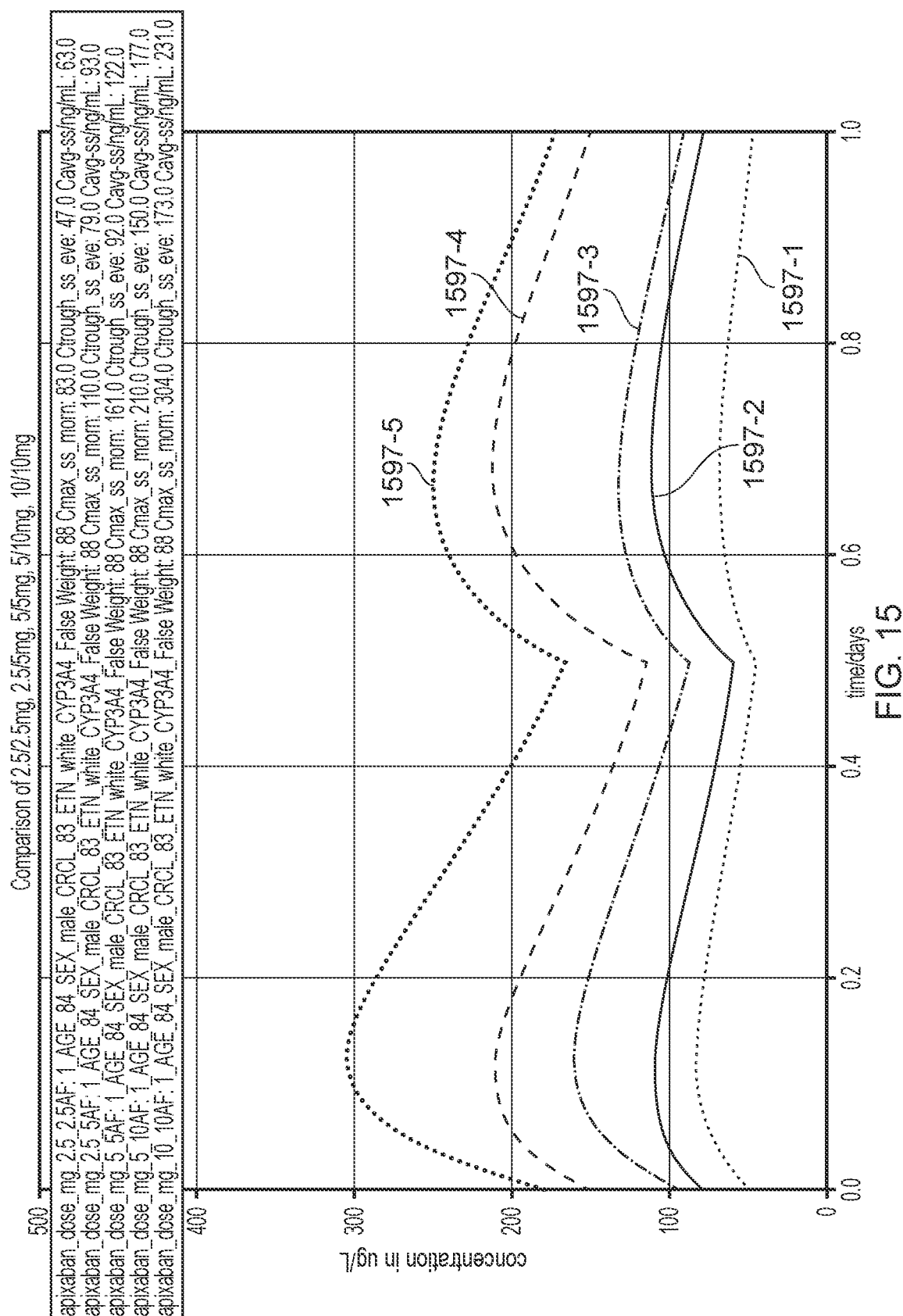
FIG. 15 illustrates simulated plasma levels for different dosages for an example patient using a dosage calculator according to an embodiment of the present disclosure.

FIG. 15 illustrates simulated plasma levels for different dosages for NB using a dosage calculator according to an embodiment of the present disclosure. A first plot 1597-1 shows simulated steady state plasma levels for a 2.5 mg dosage of Apixaban administered twice daily to NB. Total area under the curve was 1512 ng*h/mL and the trough level in the evening was 47 ng/ml. A second plot 1597-2 shows simulated steady state plasma levels for a 2.5 mg morning dosage of Apixaban and a 5.0 evening dosage of Apixaban administered daily to NB. Total area under the curve was 2232 ng*h/mL and the trough level in the evening was 79 ng/ml. A third plot 1597-3 shows simulated steady state plasma levels for a 5.0 mg dosage of Apixaban administered twice daily to NB. Total area under the curve was 2928 ngh/mL and the trough level in the evening was 92 ng/ml. A fourth plot 1597-4 shows simulated steady state plasma levels for a 5.0 mg morning dosage of Apixaban and a 10.0 evening dosage of Apixaban administered daily to NB. Total area under the curve was 4248 ng*h/mL and the trough level in the evening was 150 ng/ml. A fifth plot 1597-5 shows simulated steady state plasma levels for a 10.0 mg dosage of Apixaban administered twice daily to NB. Total area under the curve was 5544 ngh/mL and the trough level in the evening was 173 ng/mL.

The Figure illustrates the inflexibility of current dosing guidelines and the conflict for the physicians who may disagree with the guidelines. The 2.5 mg twice daily dosing leads to a plasma level that is towards the lower end of the optimum window, potentially leaving NB vulnerable to clots. The 5.0 mg twice daily dosing leads to a plasma level towards the upper end of the optimum window, potentially leaving NB vulnerable to bleeds, a particular risk in view of the frequent falls. The 2.5 mg/5.0 mg dosing combination results in plasma levels towards the centre of the optimum window providing a good balance between the risk of clotting and bleeding. A yet further optimisation may be provided by the use of novel dosages, for example a 3.5 mg may enable the administration of the same dosage twice daily instead of requiring different dosages.

The example, dosage calculators, plasma level prediction models and methods for calculating personalised target metrics described herein are exemplary. Treatment algorithms, including computation of ideal and personalised plasma level metrics, may also be expressed by explicit rules (e.g. if . . . then . . . ), Bayesian or other statistical inference derived from population data, or via Machine Learning (e.g. Deep Learning). The type of algorithm may be selected for performance, suitability for context and governing regulatory framework. In some examples, dosage calculators and/or plasma level prediction models may be refined continuously as new data is accumulated or revised periodically for regulatory approval according to governance requirements and patient risk.

Figure 16:
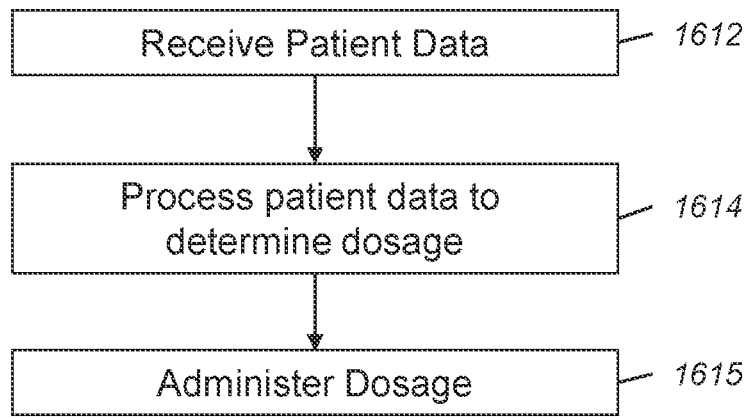
FIG. 16 illustrates a method for administering a dosage of Apixaban to a patient for the treatment or prevention of thrombosis according to an embodiment of the present disclosure.

FIG. 16 illustrates a method for administering a dosage of apixaban to a patient for the treatment or prevention of thrombosis.

A third step 1615 of the method comprises administering a dosage of apixaban to the patient. The dosage is determined by: a first step 1612 comprising receiving patient data relating to a patient, wherein the patient data includes a kidney function metric of the patient; and a second step comprising processing, using one or more processors, the patient data with a dosage calculator to determine the dosage of apixaban for the patient, wherein the dosage calculator is derived from a plasma level prediction model that predicts Apixaban drug plasma levels, and the dosage calculator determines the dosage for the patient based in part on the kidney function metric of the patient.

Figure 17:
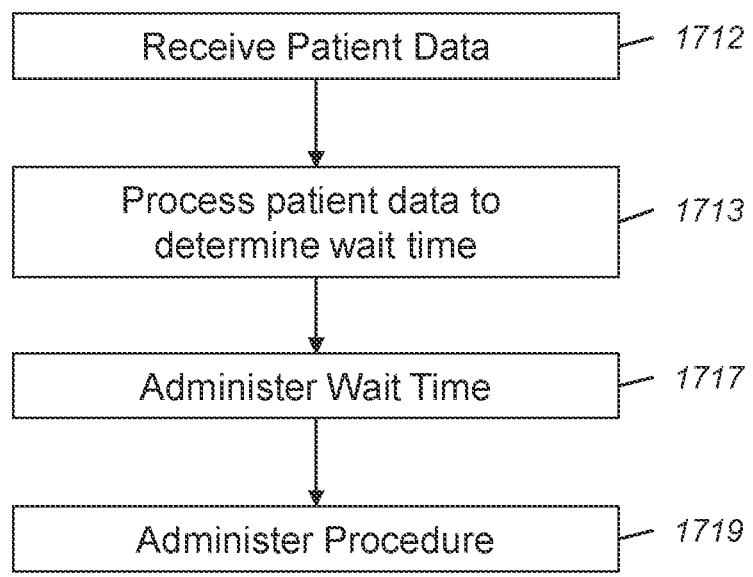
FIG. 17 illustrates a method for determining and administering a procedure wait time for a patient following withdrawal of a direct oral anti-coagulant in advance of an invasive procedure according to an embodiment of the present disclosure.

FIG. 17 illustrates a method for determining and administering a procedure wait time for a patient following withdrawal of a direct oral anti-coagulant (DOAC) in advance of an invasive procedure.

A first step 1712 comprises receiving patient data relating to a patient, wherein the patient data includes a kidney function metric of the patient and a DOAC dosage for the patient.

A second step 1713 comprises processing, using one or more processors, the patient data with a dosage calculator to determine the procedure wait time for a drug plasma level to fall below an invasive procedure plasma level threshold, wherein the dosage calculator is derived from a plasma level prediction model that predicts DOAC drug plasma levels, and the dosage calculator determines the procedure wait time for the patient based in part on the kidney function metric of the patient A third step 1717 comprises administering the procedure wait time in advance of the invasive procedure to reduce a risk of haemorrhage during the invasive procedure.

An optional fourth step 1719 comprises administering or performing the invasive procedure on the patient.

Throughout the present specification, it will be appreciated that any reference to "close to", "before", "shortly before", "after" "shortly after", "higher than", or "lower than", etc, can refer to the parameter in question being less than or greater than a threshold value, or between two threshold values, depending upon the context.

[1]: Apixaban FDA SBA 202155 Clinical Pharmacology (2012)

[2]: Byon W, Garonzik S, Boyd R A, Frost C E. Apixaban: A Clinical Pharmacokinetic and Pharmacodynamic Review. Clin Pharmacokinet. 2019 October; 58 (10): 1265-1279. doi: 10.1007/s40262-019-00775-z. PMID: 31089975; PMCID: PMC6769096.

[3]: Frost C, Wang J, Nepal S, Schuster A, Barrett Y C, Mosqueda-Garcia R, et al. Apixaban, an oral, R, et al. Apixaban, an oral, direct factor Xa inhibitor: single dose safety, pharmacokinetics, pharmacodynamics and food effect in healthy subjects. Br J Clin Pharmacol. 2013; 75 (2): 476-87.

[4]: Raghavan N, Frost C E, Yu Z, He K, Zhang H, Humphreys W G, Pinto D, Chen S, Bonacorsi S, Wong P C, Zhang D. Apixaban metabolism and pharmacokinetics after oral administration to humans. Drug Metab Dispos, 2009 January; 37 (1): 74-81. doi: 10.1124/dmd.108.023143. Epub 2008 Oct. 2. PMID: 18832478.

[5]: ELIQUIS PIL FDA 2012 https://www.accessdata.fda.gov/drugsatfda_docs/label/2012/202155s000lbl.pdf

[6]: ELIQUIS 5.0 mg SPC. Last updated April 2016. <http://www.ema.europa.eu/docs/en_GB/document_library/EPAR_-Product_Information/human/002148/WC500107728.pdf>2016.

[7]: de Vries T A C, Hirsh J, Xu K, Mallick I, Bhagirath V C, Eikelboom J W, Ginsberg J S, Kruger P C, Chan N C. Apixaban for Stroke Prevention in Atrial Fibrillation: Why are Event Rates Higher in Clinical Practice than in Randomized Trials?—A Systematic Review. Thromb Haemost. 2020 September; 120 (9): 1323-1329. doi: 10.1055/s-0040-1713889. Epub 2020 Jul. 15. PMID: 32668484.

[8]: Cirincione B, Kowalski K, Nielsen J, Roy A, Thanneer N, Byon W, et al. Population pharmacokinetics of apixaban in subjects with non-valvular atrial fibrillation. CPT Pharmacometrics Syst Pharmacol. 2018; 7 (11): 728-38

[9]: Ueshima, S., Hira, D., Fujii, R., Kimura, Y., Tomitsuka, C., Yamane, T., et al. (2017). Impact of ABCB1, ABCG2, and CYP3A5 polymorphisms on plasma trough concentrations of apixaban in Japanese patients with atrial fibrillation. Pharmacogenet. Genomics 27 (9), 329-336. doi: 10.1097/FPC.

[10]: Merli, Geno J.; Kraft, Walter K.; Eraso, Luis H.; Galanis, Taki; Thomson, Lynda J.; Ouma, Geoffrey O.; Viscusi, Eugene; Gong, Jerald Z.; and Lam, Edwin, "Apixaban Discontinuation for Invasive or major Surgical procedures (ADIOS): A prospective cohort study." (2021). Department of Medicine Faculty Papers. Paper 315. https://jdc.jefferson.edu/medfp/315

The invention claimed is:

1. A method for determining and administering a procedure wait time for a patient following withdrawal of a direct oral anti-coagulant, DOAC, in advance of an invasive procedure, the method comprising:
receiving patient data relating to a patient, wherein the patient data includes a kidney function metric of the patient and a DOAC dosage for the patient;
processing, using one or more processors, the patient data with a dosage calculator to determine the procedure wait time for a drug plasma level to fall below an invasive procedure plasma level threshold, wherein the dosage calculator is derived from a plasma level prediction model that predicts DOAC drug plasma levels, and the dosage calculator determines the procedure wait time for the patient based in part on the kidney function metric of the patient; and
administering the procedure wait time in advance of the invasive procedure to reduce a risk of haemorrhage during the invasive procedure.

2. The method of claim 1, wherein after administering the procedure wait time, the method comprises administering the invasive procedure on the patient.

3. The method of claim 1, wherein the patient data further comprises one or more of: a patient age; a patient ethnicity; a patient sex; a patient weight; a patient genotype; a patient cardiac metric; and a patient medication list of one or more medications that the patient is taking in addition to the DOAC.

4. The method of claim 3, wherein, the patient medication list in addition to the DOAC comprises an indication of whether the patient is consuming one or more medications comprising: a Cytochrome P450 3A4, CYP3A4, inhibitor; a CYP3A4 inducer; a P-glycoprotein, PGP, inhibitor; a PGP inducer; and a drug that increases a bleeding risk including a drug with an anticoagulant effect.

5. The method of claim 1, wherein the patient data further comprises one or more of: reported side-effects; alcohol intake; smoking history, a patient clotting metric; a treatment purpose; patient genetic determinants; patient co-conditions; a patient activity level; a patient dosage compliance; a patient liver function; a patient thrombosis history; a patient haemorrhage history; a patient cancer history; a family thrombosis history; familial stroke history, familial bleeding history; cardiovascular history; metabolic history; a patient blood pressure history; a patient platelet count; a patient heart rate; and a patient haematocrit.

6. The method of claim 1, wherein the DOAC comprises apixaban.

7. The method of claim 1, wherein the DOAC dosage includes a final drug dosage of the DOAC prior to drug withdrawal in advance of an invasive procedure and the method comprises:
processing the final drug dosage with the dosage calculator to determine a procedure wait time for the plasma level to fall below an invasive procedure plasma level threshold.

8. The method of claim 7, wherein the final drug dosage of the DOAC includes a dosage amount and/or a dosage time.

9. The method of claim 1, wherein the plasma level prediction model comprises a time-based differential equation model for modelling a time dependence of a plasma concentration of the DOAC as a function of the patient data.

10. The method of claim 1, wherein the dosage calculator comprises a machine learning algorithm trained using the plasma level prediction model.

11. The method of claim 10, wherein the dosage calculator comprises a machine learning dosage calculator trained using simulated population data comprising simulated patient data and simulated procedure wait times calculated with the plasma level prediction model.

12. The method of claim 11, wherein the machine learning dosage calculator is trained for a specific invasive procedure plasma level threshold or trained for a range of invasive procedure plasma level thresholds.

13. The method of claim 3, wherein patient cardiac metric comprises an indication that the patient has non-valvular atrial fibrillation.

14. The method of claim 3, wherein the patient genomic type comprises a patient genotype for Pgp transporter genes such as ABCG or metabolic enzymes such as CYP 3A4/5.

15. The method of claim 4, wherein the one or more medications in addition to the DOAC comprise one or more of:
an additional anticoagulant such as heparin, warfarin, or a direct oral anti-coagulant;
an antiplatelet such as aspirin, clopidogrel, and ticagrelor;
a CYP3A4 and/or PGP inhibitor such as itraconazole, ketoconazole, an HIV protease inhibitor, amiodarone, clarithromycin, diltiazem, fluconazole, quinidine, and verapamil;
a CYP3A4 and/or PGP inducer such as carbamazepine, phenytoin, rifampicin, and St John's Wort; and
serotonin reuptake inhibitors or serotonin norepinephrine re-uptake inhibitors.

* * * * *